United States Patent
Sagandira et al.

(10) Patent No.: US 12,319,639 B2
(45) Date of Patent: Jun. 3, 2025

(54) FLOW SYNTHESIS PROCESS FOR THE PRODUCTION OF OSELTAMIVIR

(71) Applicant: Nelson Mandela University, Port Elizabeth (ZA)

(72) Inventors: Cloudius Ray Sagandira, Port Elizabeth (ZA); Paul Watts, Port Elizabeth (ZA)

(73) Assignee: Nelson Mandela University, Port Elizabeth (ZA)

( * ) Notice: Subject to any disclaimer, the term of this patent is extended or adjusted under 35 U.S.C. 154(b) by 638 days.

(21) Appl. No.: 17/438,518

(22) PCT Filed: Feb. 28, 2020

(86) PCT No.: PCT/IB2020/051707
§ 371 (c)(1),
(2) Date: Sep. 13, 2021

(87) PCT Pub. No.: WO2020/183281
PCT Pub. Date: Sep. 17, 2020

(65) Prior Publication Data
US 2022/0144756 A1    May 12, 2022

(30) Foreign Application Priority Data
Mar. 14, 2019  (NL) ..................... 2022745

(51) Int. Cl.
*C07C 231/14*   (2006.01)
(52) U.S. Cl.
CPC ................ *C07C 231/14* (2013.01)
(58) Field of Classification Search
CPC ...... C07F 9/2466; C07F 9/564; C07C 231/12; C07C 231/14; C07C 233/52; C07C 247/14; C07C 2601/16; C07C 303/28; C07C 303/30; C07C 309/66; C07C 67/08; C07C 69/757; Y02P 20/55
See application file for complete search history.

(56) References Cited

U.S. PATENT DOCUMENTS

| | | | | |
|---|---|---|---|---|
| 2007/0197807 | A1* | 8/2007 | Gabel | C07D 303/40 560/128 |
| 2009/0076296 | A1* | 3/2009 | Trussardi | C07C 247/14 560/125 |
| 2015/0011540 | A1* | 1/2015 | Combs | A61P 11/00 514/230.2 |

FOREIGN PATENT DOCUMENTS

| | | |
|---|---|---|
| WO | 2009037137 | 3/2009 |
| WO | 2013061340 | 5/2013 |

OTHER PUBLICATIONS

Ogasawara et al. (Multistep Continuous-Flow Sysnthesis of (+)-Oseltamivir, Synthesis, 49, pp. 424-428, Published 2017) (Year: 2017).*
Ishikawa et al. (Synthesis of (+)-Oseltamivir by Using a Microreactor in the Curtis Rearrangement, Eur. J. Org. Chem., pp. 6020-6031, Published 2011) (Year: 2011).*
Brase et al. (Organic Azides: An Exploding Diversity of a Unique Class of Compounds, A Review, Agnew. Chem. Int. Ed., 44, pp. 5188-5240, Published 2005) (Year: 2005).*
Nie et al. (A Short and Practicle Synthesis of Oseltamivir Phosphate (Tamiflu) from (+)-Shikimic Acid, J. Org. Chem., 74, pp. 3970-3973, Published 2009) (Year: 2009).*
Wiles et al. (Recent advances in micro reaction technology, Chem. Commun., 47, pp. 6512-6535, Published 2011) (Year: 2011).*
International Search Report based on co-pending International Application No. PCT/IB2020/051707, dated Jun. 9, 2020—pp. 1-3.
International Preliminary Report on Patentability dated Jun. 14, 2021 based on co-pending Interntional Application No. PCT/IB2020/051707—pp. 1-6.

* cited by examiner

*Primary Examiner* — Yevgeny Valenrod
*Assistant Examiner* — Blaine G Doletski
(74) *Attorney, Agent, or Firm* — McCarter & English, LLP

(57) ABSTRACT

This invention provides for a flow synthesis process for producing Oseltamivir and pharmaceutically acceptable salts thereof from shikimic acid in particular but not exclusively to a flow synthesis process for producing Oseltamivir phosphate from shikimic acid in a nine-step flow synthesis that provides for superior reaction times and product yields compared to known methods.

20 Claims, 17 Drawing Sheets

FLOW SYNTHESIS PROCESS FOR THE PRODUCTION OF OSELTAMIVIR

CROSS-REFERENCE TO RELATED APPLICATIONS

This application is a national stage application filed under 35 U.S.C. § 371 of PCT/IB2020/051707, filed Feb. 28, 2020, which claims the benefit of Netherlands Patent Application No. 2022745, filed Mar. 14, 2019, all of which are incorporated herein, in their entireties, by reference.

INTRODUCTION

This invention relates to a process for producing Oseltamivir and pharmaceutically acceptable salts thereof, in particular to a flow synthesis process for producing this compound.

BACKGROUND

Influenza is a severe viral infection of the respiratory system, which is responsible for significant morbidity and mortality due to both annual epidemics and predictable pandemics. In the United States alone, 200000 hospitalizations and 36000 deaths are recorded per year. In addition, annually the virus affects around 20% of the world population, resulting in about 500000 deaths.

Oseltamivir phosphate, a compound in the class of compounds referred to as neuraminidase inhibitors (NAIs), is used in the treatment and prophylaxis of influenza. It is effective against influenza caused by both the influenza A and influenza B viruses.

There are numerous processes and synthetic routes described in the prior art for the preparation of Oseltamivir phosphate.

However, existing synthesis methodologies for the production of these compounds have essentially been based on standard stirred batch reactor type processes, wherein significant volumes of organic solvents are used. In addition, most of the known processes either employ azide chemistry or protecting group chemistry, both of which introduce inherent limitations, in particular in batch processes.

EP 2 193 116 describes such a batch method for a process of producing Oseltamivir phosphate from shikimic acid. The methodology employed is that of a typical batch process, with no suggestion that it may be desirable to attempt to develop a flow synthesis process based on the methods, reagents, and reaction conditions disclosed therein. Further, there is no indication of how the steps disclosed in this application may be adapted and improved to arrive at a flow synthesis method that is superior in both reaction times and reaction yields.

Azide chemistry poses many safety concerns because of its hazardous and highly exothermic nature, which becomes even more pronounced at an industrial scale. Due to these inherent dangers, the process chemist is limited in the reaction parameters that can be employed to maximise reaction efficiency and reaction yield. Protecting group chemistry, on the other hand, generally increases reaction time whilst reducing overall yield, thereby increasing final product cost.

Micro reactor technology (MRT), more recently branded 'flow chemistry', is an emerging technique that enables those working in research and development to rapidly screen reactions utilising continuous flow, leading to the identification of reaction conditions that are suitable for use at a production level. Furthermore, in addition to using conventional reaction methodology, the inherent safety associated with the use of small reactor volumes enables users to employ reaction conditions previously thought to be too hazardous for use within a production environment; such as extreme reaction conditions or the use/generation of 'hazardous' compounds. Consequently, the type of reactions available to the chemist increases through the use of this technology.

Furthermore, in the case of Oseltamivir phosphate, continuous flow synthesis may potentially provide a technology that is efficient enough to enable rapid local manufacture in the event of a pandemic, in particular in developing countries.

The present invention seeks to address some of the shortcomings of the prior art by providing new flow chemistry processes for the production of Oseltamivir.

SUMMARY OF THE INVENTION

According to a first aspect to the present invention there is provided a flow synthesis process for producing a compound of the Formula 33 and its pharmaceutically acceptable salts,

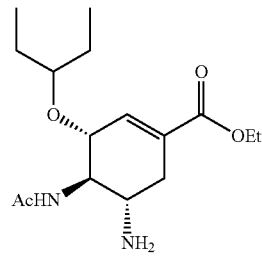

33 the process comprising the steps of:
a) preparing ethyl shikimate of Formula 39

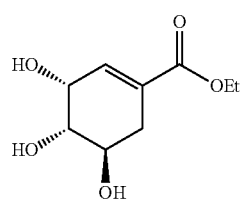

39 by reacting shikimic acid with a reagent selected from the group consisting of (COCl)$_2$, SOCl$_2$, benzene sulphonic acid (BSA), p-toluene sulphonic acid (PTSA), and Amberlyst 15, b) reacting the ethyl shikimate of Formula 39 with mesyl chloride in the presence of a base selected from the group consisting of trimethyl amine (TEA), 1,8-diazabicyclo(5.4.0) undec-7-ene (DBU), imidazole, and trihexyl amine (THA) to produce the O-trimesylate of Formula 40

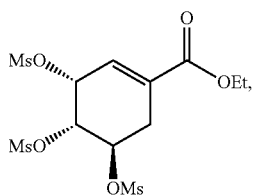

40 c) reacting the O-trimesylate of Formula 40 in an azidation reaction with an appropriate azidating agent to produce the azide of Formula 41

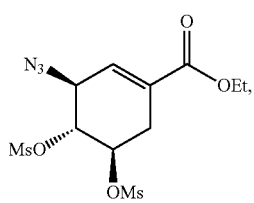

41 d) reacting the azide of Formula 41 in an aziridation reaction with a trialkyl phosphite to produce the aziridine of Formula 42

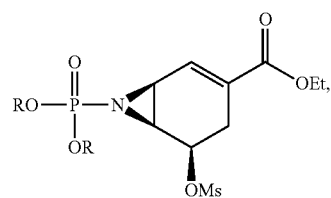

42 e) reacting the aziridine of Formula 42 with 3-pentanol in the presence of a Lewis acid catalyst to produce the 3-pentyl ether of Formula 43

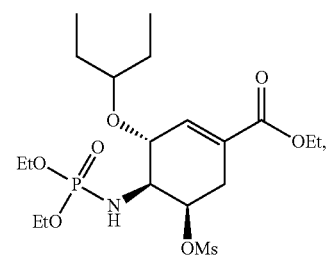

43 f) reacting the 3-pentyl ether of Formula 43 in an acetylation reaction with $H_2SO_4$, followed by $Ac_2O$ in the presence of a suitable base to produce the acetamide of Formula 44

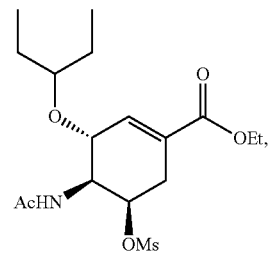

44 g) reacting the acetamide of Formula 44 in an azidation reaction with an appropriate azidating reagent produce the azide of Formula 32

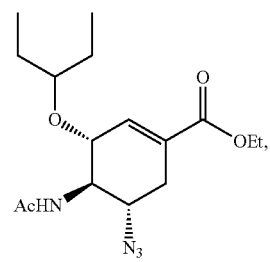

32 and h) reacting the azide of Formula 32 by mixing the azide with $CoCl_2$, and reacting the mixture with $NaBH_4$ to produce the compound of Formula 33.

Preferably, the process further comprises reacting the compound of Formula 33 with phosphoric acid to produce the compound of Formula 3

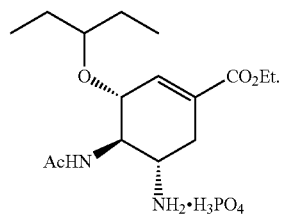

3

Preferably, in step (a) shikimic acid is reacted with $(COCl)_2$ or Amberlyst 15.

In one embodiment, in step (a) shikimic acid is reacted with $COCl_2$ at a temperature of between about 120° C. and about 170° C.

In another embodiment, in step (a) shikimic acid is reacted with Amberlyst 15 at a temperature of between about 100° C. and about 145° C.

In one embodiment, the reaction in step (b) proceeds at room temperature.

In a preferred embodiment, the reaction in step (b) proceeds under sonication. Preferably, in step (b) the base is present at a concentration of about 8 to about 20 molar equivalents relative to ethyl shikimate.

In one embodiment, in step (c) the azidation reaction is performed with $NaN_3$ at a concentration of about 1.1 molar equivalents relative to the O-trimesylate of Formula 40.

In a preferred embodiment, in step (c) the azidation reaction is performed with $NaN_3$ at a temperature of about 50° C.

Preferably, in step (d) the trialkyl phosphite is selected from triethyl phosphite and trimethyl phosphite.

In a preferred embodiment, in step (d) the reaction is performed in acetonitrile at a temperature of between about 150° C. to about 190° C.

In a preferred embodiment, in step (e) the reaction is performed at a temperature of between about 60° C. to about 100° C.

Preferably, wherein in step (f) the reaction of the 3-pentyl ether with $H_2SO_4$ is performed at a temperature of between about 140° C. to about 180° C.

Preferably, in step (g) the reaction is performed at a temperature of between about 140° C. to about 200° C.

In one embodiment, in step (h) the reaction is performed at about room temperature.

In a preferred embodiment, in step (h) the reaction is performed under sonication.

BRIEF DESCRIPTION OF THE DRAWINGS

The invention will now be described in more detail with reference to the following non-limiting embodiments and figures in which.

DETAILED DESCRIPTION OF A PREFERRED EMBODIMENT

Figure 1:
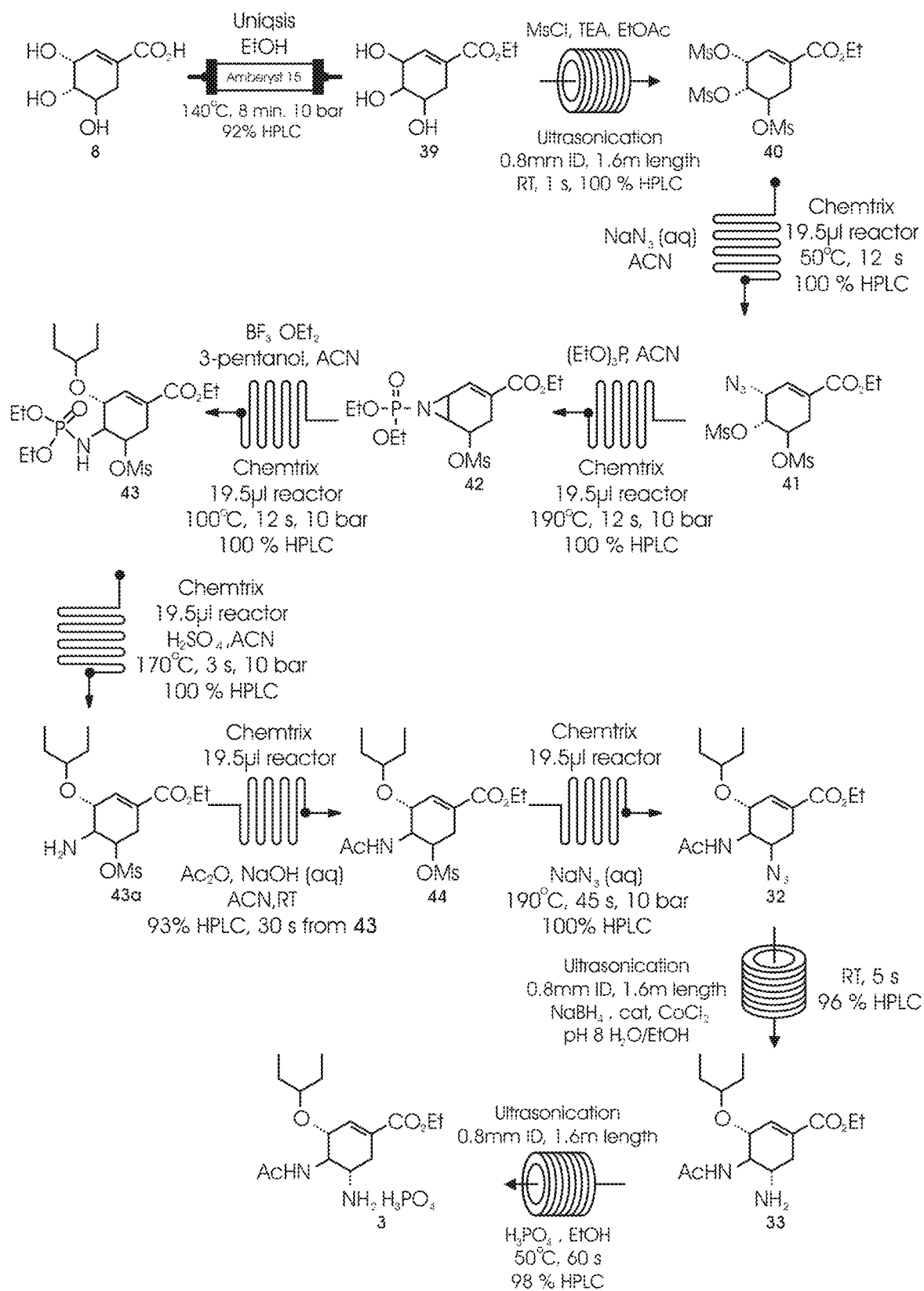
FIG. 1 shows one example of an optimised synthetic route for a continuous flow synthesis process for producing Oseltamivir phosphate.

The present invention will now be described more fully hereinafter with reference to the accompanying figures, in which some of the non-limiting embodiments of the invention are shown.

The invention as described hereinafter should not be construed to be limited to the specific embodiments disclosed, with slight modifications and other embodiments intended to be included within the scope of the invention.

Although specific terms are employed herein, they are used in a generic and descriptive sense only and not for purposes of limitation.

As used herein, throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having", "including", and variations thereof used herein, are meant to encompass the items listed thereafter, and equivalents thereof as well as additional items.

The present invention provides for a process for producing Oseltamivir and pharmaceutically acceptable salts thereof, in particular to a flow synthesis process for producing this compound. In a particularly preferred embodiment, the invention provides for a flow synthesis process for producing a pharmaceutically acceptable salt of Oseltamivir, (−)-Oseltamivir phosphate commonly referred to under the brand name Tamiflu®.

The invention provides for a continuous flow synthesis process for producing Oseltamivir and pharmaceutically acceptable salts thereof, that does not include the use of rate and yield limiting protecting group chemistry. As a consequence of avoiding protecting group chemistry, we have developed a continuous flow procedure that is high yielding and extremely efficient. In a preferred embodiment of the invention, a 10 steps continuous flow procedure towards Oseltamivir phosphate 3 is provided having an overall yield of 80.5% in a total residence time of 11 min.

General Experimental Procedures

Chemicals were supplied by Sigma Aldrich, Merck and Industrial Analytical and were used as received. Anhydrous solvents were supplied by Sigma Aldrich, and maintained by drying over appropriately activated molecular sieves during use.

Column chromatography was performed using Fluka Chemie silica gel 60 as the stationary phase, and mixtures of ethyl acetate and hexane of varying polarity were used as the mobile phase. Unless otherwise stated, thin layer chromatography (TLC) was done using Merck Kieselgel 60 HF254 aluminium backed TLC plates with mixtures of ethyl acetate and hexane of varying polarity as eluent. TLC visualisation was done by fluorescence on exposure to short wave ultra violet (UV) light (λ 254 nm) in a Camag UV cabinet.

Nuclear magnetic resonance (NMR) spectra were recorded at room temperature as solutions in deuterated chloroform ($CDCl_3$) or deuterated dimethyl sulfoxide (DMSO-$d_6$). A Bruker Avance-400 spectrometer (400 MHZ) was used to record the spectra and the chemical shifts are reported in parts per million (ppm) with coupling constants in Hertz (Hz). Infra-red spectra were recorded from 4000 to 500 $cm^{-1}$ using a Bruker spectrometer and peaks ($V_{max}$) reported in wavenumbers ($cm^{-1}$). Melting points of all compounds were determined using a Staurt$^d$ Melting Point Apparatus SMP30. High performance liquid chromatography (HPLC) data was obtained using Agilent 1200 with a UV/Vis detector and Agilent Zorbax C18-column.

HPLC Method A

HPLC analysis was performed on Agilent Zorbax C18-column (250 mm×4.6 mm, i.d. 5 μm) ambient temperature using an isocratic system. The mobile phase consisted of 70% acetonitrile and 30% water. The sample injection volume was 5 μl, eluted at a flow rate of 1.5 ml/min and detected at 213 nm with a run time of 15 min.

HPLC Method B

HPLC analysis was performed on Agilent Zorbax C18-column (250 mm×4.6 mm, i.d. 5 μm) ambient temperature using an isocratic system. The mobile phase consisted of 60% acetonitrile and 40% water. The sample injection volume was 5 μl, eluted at a flow rate of 1 ml/min and detected at 213 nm with a run time of 6 min.

The continuous flow systems used in the present invention are described below.

Labtrix Start System (Chemtrix)

This is a manually operated, 'plug and play' continuous flow reactor system for rapid reaction screening and process optimisation within a micro reactor. The system has a modular set up which facilitates the exchange of components to increase chemical compatibility, number of feed lines or reactor type or volume. It can be used to perform reactions at temperatures ranging from −20° C. to 195° C. and maximum operating pressure of 20 bar using very little reagents. This system consists mainly of a Labtrix start unit, thermo-controller, syringe pumps, syringes, tubing and fittings. The start unit holds of the micro reactor. It can be heated or cooled to temperatures between −20° C. and +195° C. which is controlled by a thermo-controller. Syringe pump fitted with glass gas tight Leur lock syringes dose reagents into the microreactors. There are twelve different interchangeable glass micro reactor types available this system which differ in volume and design. These glass reactors have three distinct categories depending on their design and mixing patterns. T-mixer reactors, SOR-mixer reactors and catalyst reactors are the three categories.

Uniqsis Packed Bed Flow Column Reactor System

The system consisted of a 10 mm i.d.×100 mm Omnifit glass column with enhanced PEEK adjustable end fittings. PTFE tubing (0.8 mm ID) was used to connect the column reactor to the HPLC pump and from the reactor to the collecting vessel. A peristaltic HPLC pump, Series III (10 ml pump head) with flow rate range of 0.00-10.00 ml/min was used to dose the liquid reagent through the packed column reactor which was fitted with a 10 bar back pressure regulator. Uniqsis heating holder was used for heating the glass column reactor.

Sonicated PTFE Coil Reactor System

The system consisted of a Chemyx syringe pump fitted with two 10 ml SGE glass syringes filled with reagents. The two streams of reagents were pumped into a T-mixer (Omnifit labware, Pore size: 8.0 mm ID, 0.5-4 mm OD) which was connected to a 0.8 ml PTFE coil reactor (0.8 mm ID, 1.6 ml tube length) with a product collection vial downstream. The T-mixer and the PTFE coil reactor were placed into a temperature controlled sonicated water bath. EINS SCI professional ultrasonic bath (40 kHz) was used for sonication.

Reaction 1: Continuous Flow Esterification of Shikimic Acid 8

Figure 21:
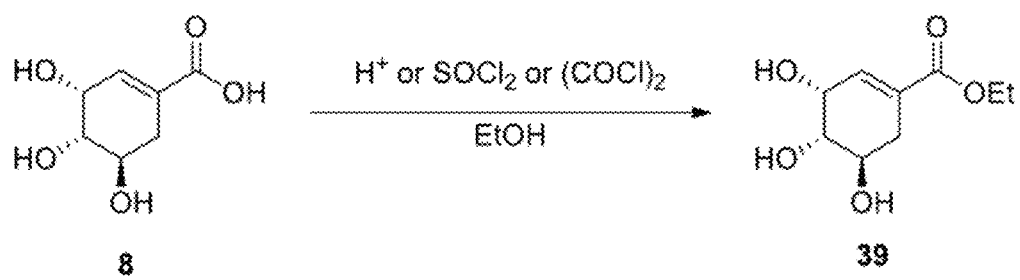
FIG. 21 shows the reaction scheme for the esterification Shikimic acid 8.

Shikimic acid 8 esterification is the first step in the synthesis of (−)-Oseltamivir phosphate (FIG. 21). Various esterification conditions were investigated to optimise the esterification reaction in Chemtrix Labtrix and Uniqsis packed bed column flow systems. All the solution phase and solid phase esterification were done in a Chemitrix Labtrix system, and Uniqsis packed bed column reactor, respectively.

A Chemtrix Labtrix system was used to perform all solution phase esterification investigations. The system, fitted with a 19.5 μl glass reactor, was used for shikimic acid esterification optimisation in the presence of catalyst. Thionyl chloride, oxalyl chloride, thionyl chloride/DMF, oxalyl chloride/DMF, benzene sulphonic acid (BSA) and p-Toluene sulphonic acid (PTSA) were the various catalyst investigated for shikimic acid esterification. Two syringe pumps were used to pump reagents from two 10 ml SGE Luer lock gas tight glass syringes into the thermally controlled microreactor system which was fitted with a 10 bar back pressure regulator. Shikimic acid (0.1 M) and catalyst were both dissolved in ethanol and pumped into the flow system separately. Samples were collected and analysed using HPLC method A.

Figure 22:
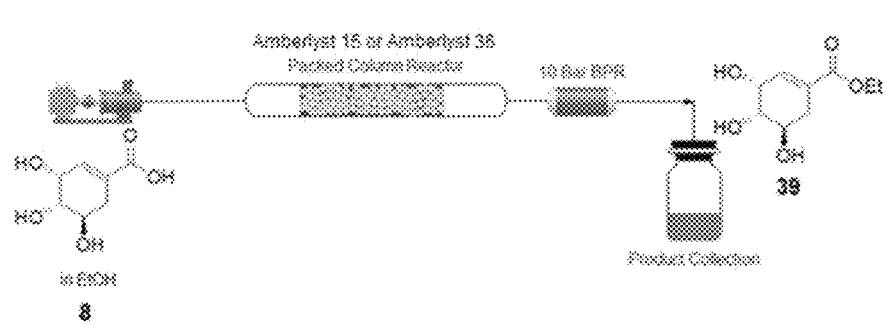
FIG. 22 shows a schematic representation of the column reactor used all for solid phase esterification investigations.
Figure 23:
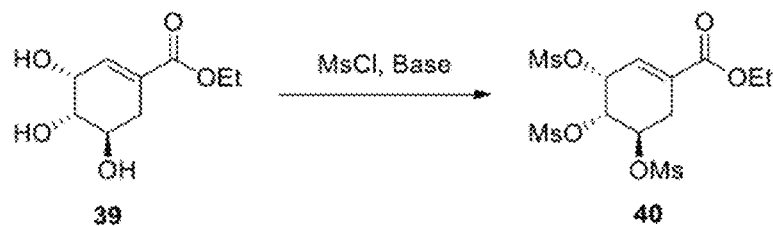
FIG. 23 shows the reaction scheme for the mesylation of Ethyl shikimate 39.

A Uniqsis column reactor packed with a solid catalyst was used all for solid phase esterification investigations (FIG. 22).

A 10 mm ID×100 mm Uniqsis glass column was packed with Amberlyst 15 or Amberlyst (3 cm bed height, 2.4 reactor volume). The column reactor was heat controlled using Uniqsis heating mantle, and the system was pressurised using a 10 bar back pressure regulator. A peristaltic HPLC pump was used to pump a solution of shikimic acid (0.1 M) in ethanol into the heated packed bed. Samples were collected and analysed using HPLC method A.

The results and discussions of the detailed investigations on the use of $SOCl_2$, $COCl_2$, BSA, PTSA, Amberlyst 15 and Amberlyst 36 in continuous flow shikimic acid esterification optimisation is reported herein.

Shikimic acid 8 esterification with ethanol in the presence of $SOCl_2$ was done in a 19.5 μl glass micro reactor system. Shikimic acid 8 (0.1 M in ethanol was treated with $SOCl_2$ (0.05 M, effectively 1 equiv.) at 100° C. and 8 min residence time. Ethyl shikimate 39 was successfully formed (68%). Doubling residence time resulted in a 6% conversion increase. Increasing temperature to 140° C. and keeping residence time at 8 min gave 79% conversion. A comprehensive reaction optimisation study was carried out after successful preliminary experiments. The effect of $SOCl_2$ equivalence, reaction temperature and residence time were investigated. An investigating into the effect of $SOCl_2$ molar equivalents on the reaction at 100° C. and 8 min residence time is shown in FIG. 2.

Figure 2:
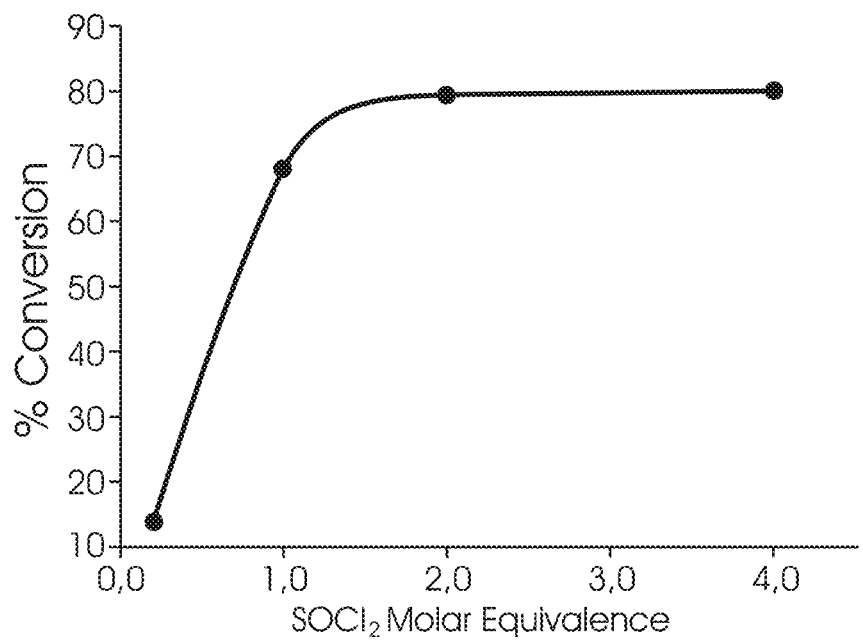
FIG. 2 shows the effect of $SOCl_2$ equivalents on shikimic acid esterification.

FIG. 2 illustrates that shikimic acid 8 conversion towards ethyl shikimate 39 generally increased with increase in $SOCl_2$ concentration. Constant % conversion was achieved at $SOCl_2$ molar equivalents of 2 and above. Without thereby wishing to be bound by any particular theory, it is believed that the excess $SOCl_2$ may be necessary because it acts as a catalyst and a water scavenger. At this determined optimum $SOCl_2$ molar equivalence, the effect of residence time and temperature was investigated (FIG. 3).

Figure 3:
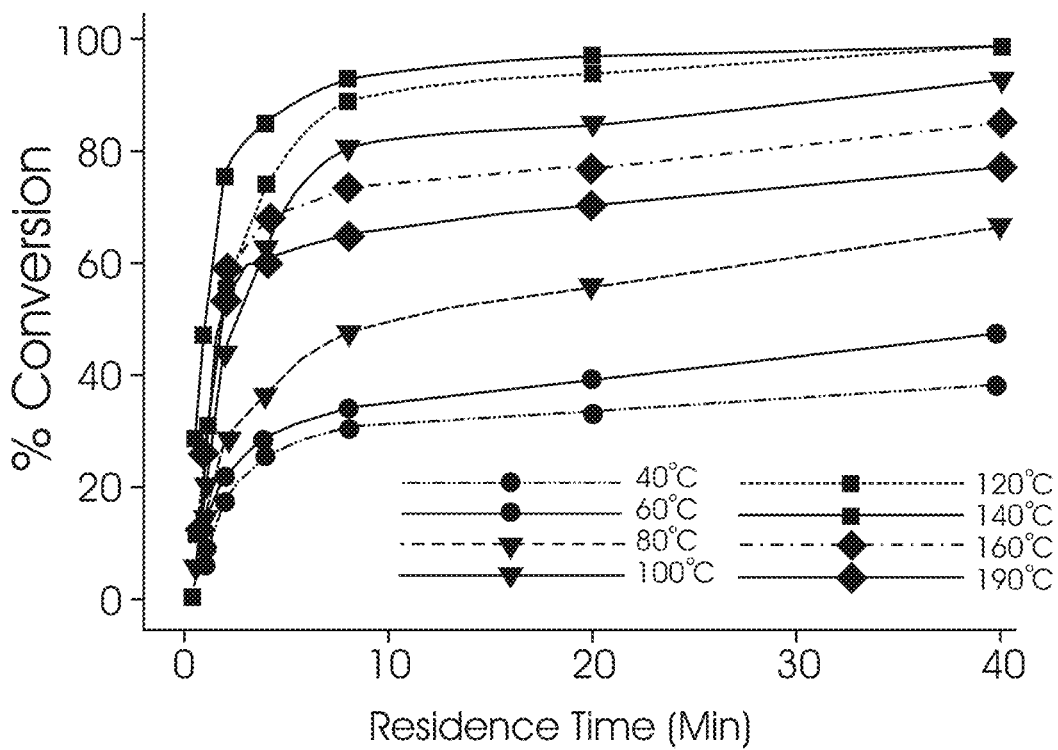
FIG. 3 shows the effect of residence time on shikimic acid esterification using $SOCl_2$ in excess.

Generally, shikimic acid 8 conversion towards ethyl shikimate 39 increased with increase in residence time and temperature (FIG. 3). However, at residence time above 8 min, further increase in residence time had limited effect on shikimic acid conversion. Furthermore, at temperatures above 140° C., shikimic acid conversion decreased. Pressurising the continuous flow system allowed us to investigate reaction temperatures above the boiling point of the solvent/reactant ethanol.

The optimum conditions for this esterification were found to be equimolar equivalents of shikimic acid and $SOCl_2$, reaction temperature of about 140° C. and residence time of about 8 min affording ethyl shikimate (93%) compared to previously reported reaction times of up to 3 hours in batch. Although the reaction is adequate, the use of $SOCl_2$ is undesirable from an environmental, health and safety perspective.

Due to the greenhouse gas ($SO_2$ and HCl) by-products produced, and toxicity concerns associated with $SOCl_2$, its replacement is desirable from an environmental, health and safety perspective.

In an attempt to develop a greener process, the use of $(COCl)_2$ as the catalyst in shikimic acid esterification was investigated. Shikimic acid 8 was esterified with ethanol in the presence of $(COCl)_2$ to afford ethyl shikimate 39. Reaction optimisation was done in a 19.5 μl glass micro reactor system. Shikimic acid (0.1 M) in ethanol was treated with $(COCl)_2$ (0.1 M, effectively 2 equiv.) in a continuous flow system.

Figure 4:
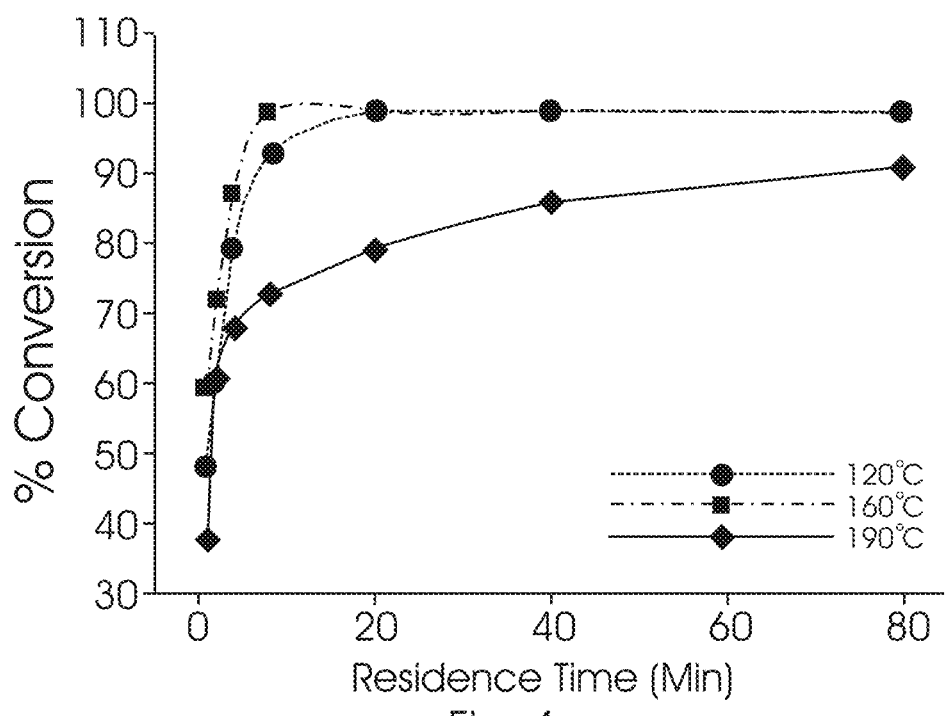
FIG. 4 shows shikimic acid esterification using $(COCl)_2$ in a continuous flow system.

There is a general increase in shimikic acid conversion as residence time and temperature increases (FIG. 4). However, shikimic acid conversion decreased at 190° C. For example, there was 73% shikimic acid conversion at 190° C. and 8 min residence time compared to a surprising conversion of 99% at 160° C. and 8 min residence time. The optimum conditions for shikimic acid esterification in the presence of $(COCl)_2$ were found to be about 120° C. to about 170° C., preferably about 120° C. to about 160° C., most preferably about 160° C., and at about 8 min residence time to afford an unexpected conversion of 99%. Under these conditions, $(COCl)_2$ proved to be a better esterification catalyst than $SOCl_2$ (93%, 140° C. and 8 min residence time). In addition, the use of $(COCl)_2$ is more desirable since it is safer and more environmentally friendly than $SOCl_2$.

We also investigated the use of $(COCl)_2$ in the presence of catalytic amount of DMF, which forms a Vilsmeier reagent which is reported to be a better carboxylic acid activator. However, results showed that the DMF catalysed procedure resulted in unexpectedly lower shikimic acid conversion than the uncatalysed reaction.

Esterification of shikimic acid with ethanol in a continuous flow system using benzene sulphonic acid (BSA) was investigated. Shikimic acid (0.1 M, 1 equiv.) in ethanol was treated with BSA (0.1 equiv.) in a continuous flow system. The results are shown in FIG. 5.

Figure 5:
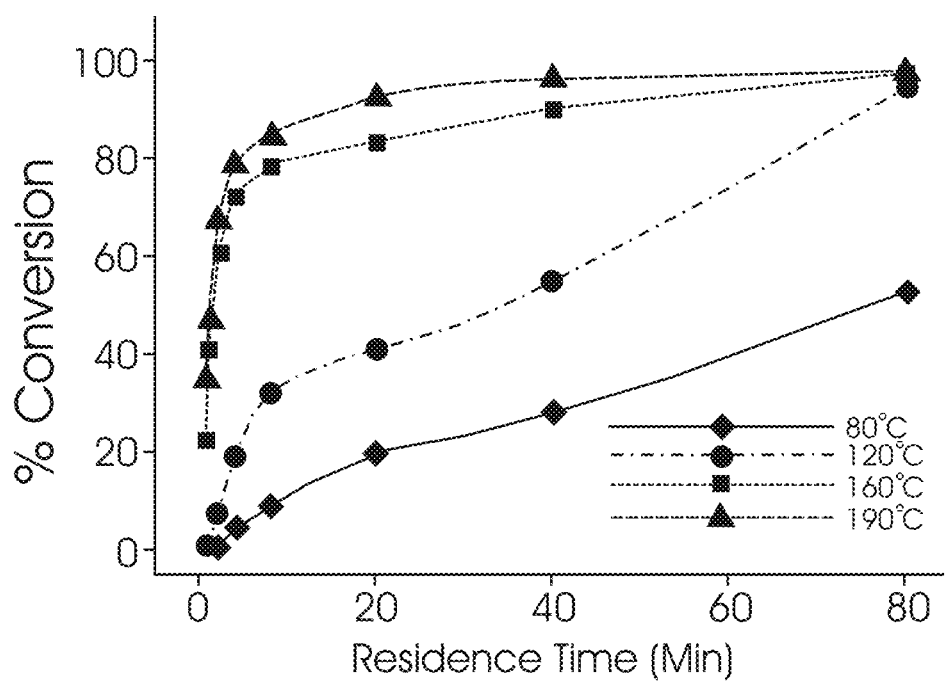
FIG. 5 shows the continuous flow shikimic acid esterification optimisation using BSA.

As can be seen from FIG. 5, an increase in both residence time and temperature resulted in an increase in shikimic acid conversion, with a conversion plateau at 98%. Furthermore, the use of highly anhydrous ethanol was preferred for this shikimic acid esterification procedure to afford high conversions. The optimum conditions for shikimic acid Fischer esterification using BSA were found to be about 190° C. and about 20 min residence time affording 94% shikimic acid conversion. Although slightly more efficient, from a health, environmental and safety perspective, BSA may be considered a more desirable esterification catalyst than $SOCl_2$.

Figure 6:
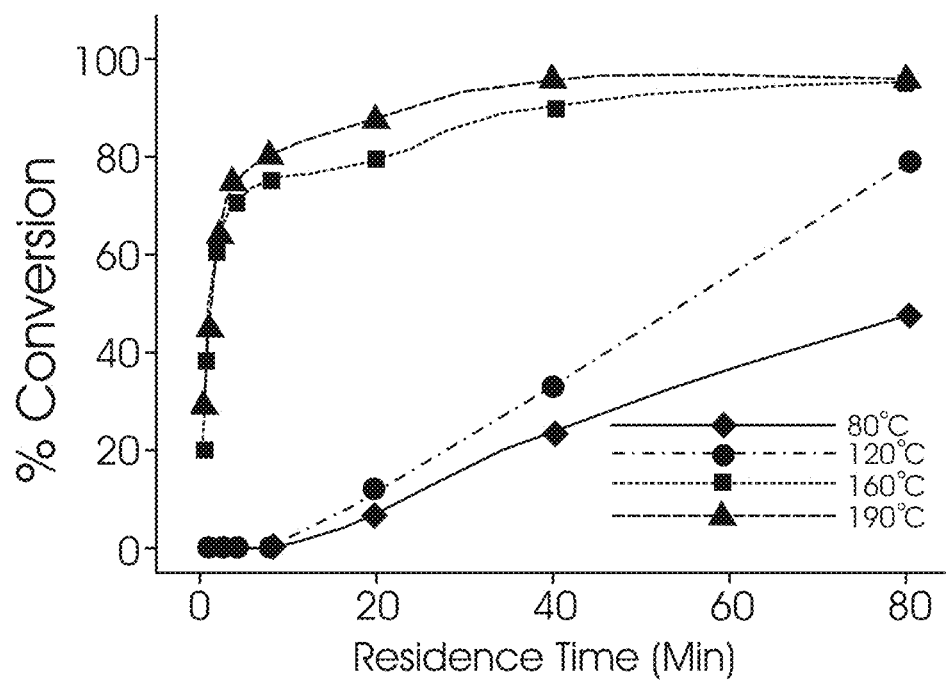
FIG. 6 shows the continuous flow shikimic acid esterification optimisation using PTSA.

The use of PTSA as a catalyst for shikimic acid esterification with ethanol in a continuous flow system was investigated. Shikimic acid (0.1 M) in ethanol was treated with catalytic amount of PTSA (0.1 equiv.) in a continuous flow system to afford ethyl shikimate 39. The results are shown in FIG. 6.

In the presence of catalytic amount of PTSA, shikimic acid conversion increased with increase in both residence time and temperature. Better conversions were achieved at 160° C. and above. The optimum conditions for the PTSA catalysed shikimic acid esterification were found to be about 190° C. and about 40 min residence time to afford 96% conversion. Although better reaction efficiency was observed with $SOCl_2$, from a health, environmental and safety perspective, PTSA may be considered a more desirable esterification catalyst than $SOCl_2$.

In order to avoid generating substantial quantities of acid waste, the use of a solid acid catalyst Amberlyst 15 in shikimic acid esterification with ethanol in a continuous flow system was investigated (FIG. 22).

Figure 7:
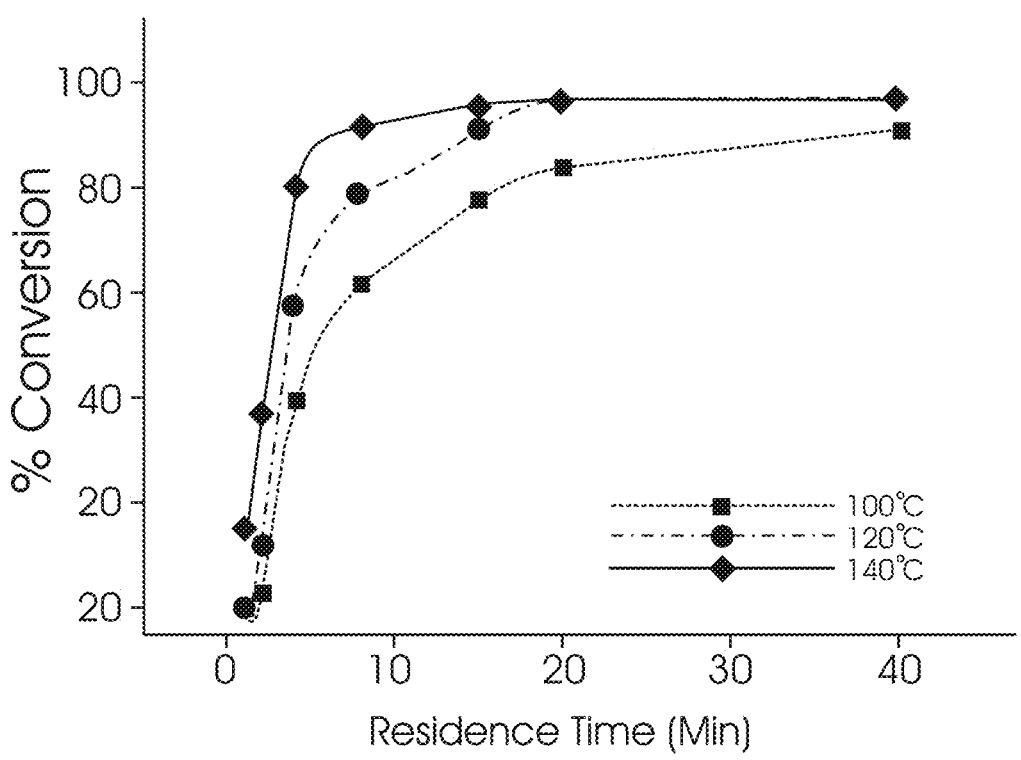
FIG. 7 shows continuous flow system for shikimic acid esterification using dry Amberlyst 15.

In the presence of dry Amberlyst 15 as the catalyst for shikimic acid esterification, shikimic acid conversion increased with increase in both temperature and residence time (FIG. 7). It appears that the reaction reached a conversion plateau at about 97%. The general recommended operating temperature for Amberlyst 15 is 120° C. However, the inventors unexpectedly found that it was possible to investigate the shikimic acid esterification using Amberyst 15 at higher temperatures, including at about 140° C.

To their delight they observed better conversions at 140° C. (92% at 8 min residence time) than at 120° C. (79% at 8 min residence time). In the experimental setup, optimum conditions were found to be 140° C. and 8 min residence time to afford 92% shikimic acid conversion. This compares favourably with the optimum conditions (93%, 140° C. and 8 min residence time) found for shikimic acid esterification using $SOCl_2$. Furthermore, from a health, environmental and safety point of view, the Amberlyst 15 procedure is more desirable than the hazardous $SOCl_2$ procedure. As an additional advantage, Amberlyst 15 can be removed at the end of the reaction, and regenerated for further use. Amberlyst 36 was also evaluated. However, results showed that Amberlyst 36 requires almost twice the residence time needed for Amberlyst 15 and $SOCl_2$ to afford the same shikimic acid conversion.

Reaction 2: Continuous Flow Mesylation of Ethyl Shikimate 39

Figure 24:
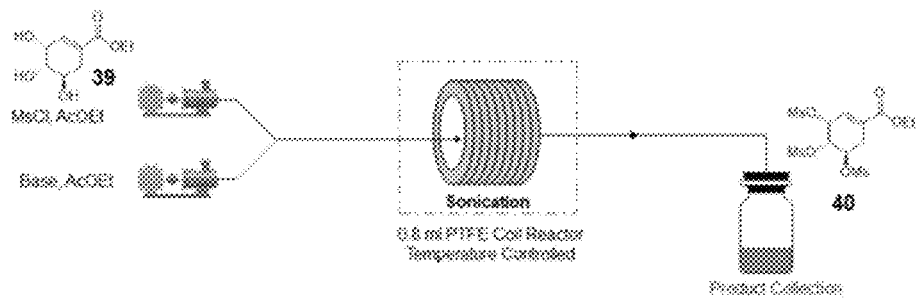
FIG. 24 shows a schematic representation of the coil reactor used all for mesylation investigations.

Ethyl shikimate 39 mesylation was performed in a 0.8 ml PTFE coil reactor system under sonication (FIG. 24).

A 0.8 ml PTFE coil reactor (0.8 mm ID, 1.6 m tube length) under sonication (FIG. 24) was used to optimise the mesylation of ethyl shikimate 39 to afford the trimesylate 40. Ethyl shikimate 39 (0.2 M) was premixed with mesyl chloride (0.9 M, 4.5 equiv.) in ethyl acetate to make the first solution. Ethyl shikimate 39 is not freely soluble in ethyl acetate. Consequently, it is dissolved in hot ethyl acetate first then cooled before premixing with mesyl chloride. The second solution was made by dissolving an organic base in ethyl acetate. The following bases were screened: triethyl amine (TEA) Imidazole, 1,8-Diazabicyclo[5.4.0]undec-7-ene (DBU), 1,4-diazabicyclo[2.2.2]octane (DABCO) and trihexylamine (THA). The samples collected were first filtered through a PTFE syringe filter (0.45 µl pore size) to remove the ammonium salts which formed during the reaction before being analysed using HPLC method B.

Ethyl shikimate 39 mesylation is reportedly done in batch type reactions using MsCl in the presence triethyl amine (TEA) as the base at low temperatures, preferably 0° C. for about 2 to 4 hours. Although mesylation transformations in batch are well established and documented, to the best of our knowledge there is no literature on continuous flow ethyl shikimate mesylation, any mesylation in a synthesis method towards Tamiflu, let alone simple model mesylation reactions.

Preliminary attempts for ethyl shikimate (0.05 M) mesylation within a 19.5 µl Chemtrix glass microreactor (300 µm channel width, 120 µm channel depth) using MsCl (0.23 M, effectively 1.5 equiv.) and TEA (5 equiv.) in ethyl acetate failed due to spontaneous blockages. These blockages were due to the ammonium salt precipitate formed between MsCl and TEA during the reaction. Experiments at lower concentrations present the same problem.

In an attempt to investigate a reactor with bigger channel diameter, we used a Little Things Factory (LTF) glass reactor with 0.8 mm channel diameter. Experiments with a simple PTFE tube coil reactor (1 mm ID) was also attempted. Disappointingly, none of these attempts solved the reactor blockage issue, even at very low concentrations.

However, in another experiment we employed a 0.8 ml PTFE coil reactor (0.8 mm ID, 1.6 m tube length) under sonication (FIG. 24). Ultrasonication appears to have assisted with movement of the ammonium salt precipitate, thereby avoiding reactor blockages. Consequently, this development enabled us to investigate different reaction parameters and ultimately reaction optimisation. It is however envisaged that ultrasonication may not necessarily be required when the reaction is scaled to industrial scale.

Ethyl shikimate b premixed with MsCl in ethyl acetate was treated with TEA in a sonicated continuous flow system affording trimesylate 40. Studies in this system were done using ethyl shikimate (0.2 M), MsCl (0.9 M, effectively 1.5 equiv.) and TEA (1.2 M, 6 equiv.) in ethyl acetate at 0° C. The effect of residence time on the reaction is shown in FIG. 8.

Figure 8:
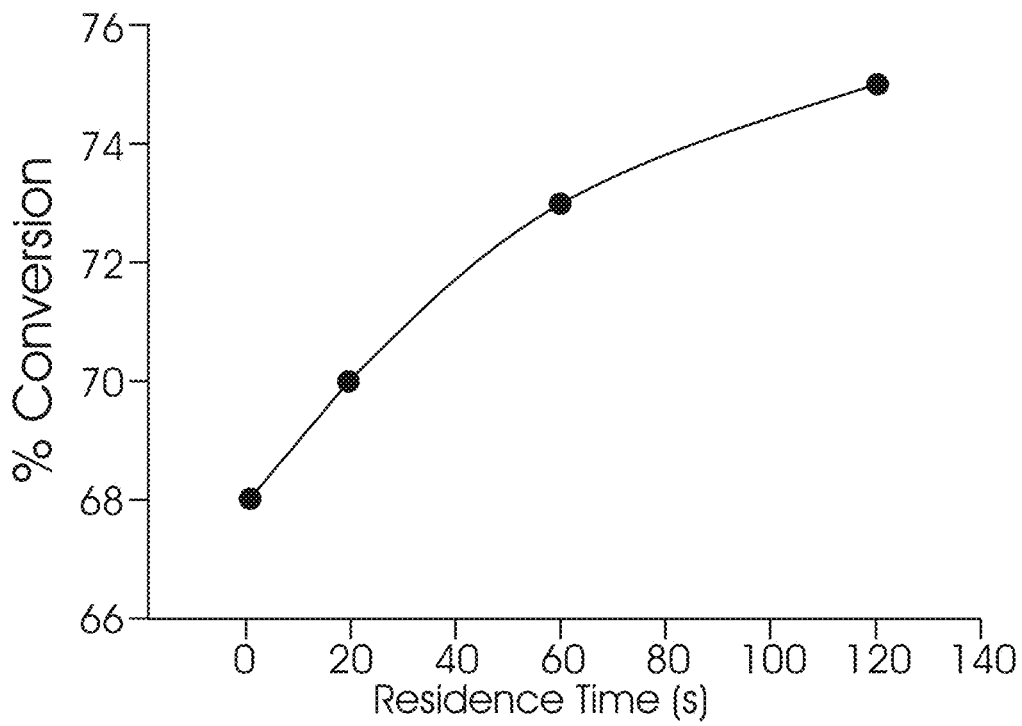
FIG. 8 shows the effect of residence time on ethyl shikimate mesylation in flow.

Ethyl shikimate conversion increased with an increase in residence time (FIG. 8). However, it was surprising to note that an increase in residence time did not significantly increase conversion as ethyl shikimate conversion. Although, the reaction is reportedly preferably done at 0° C. in batch, the use of higher temperatures to improve conversions in continuous flow systems were investigated. Room temperature and 40° C. were investigated and there was no conversion improvement. Further investigations were therefore conducted at room temperature.

Since an increase in both residence time and reaction temperature resulted in insignificant ethyl shikimate conversion, the effect of increasing base (TEA) concentration was investigated. Ethyl shikimate (0.2 M, 1 equiv.), MsCl (1.5 equiv.) at room temperature and 12 s residence time was used for these experiments whilst varying TEA concentration. The results of these experiments are shown in FIG. 9.

Figure 9:
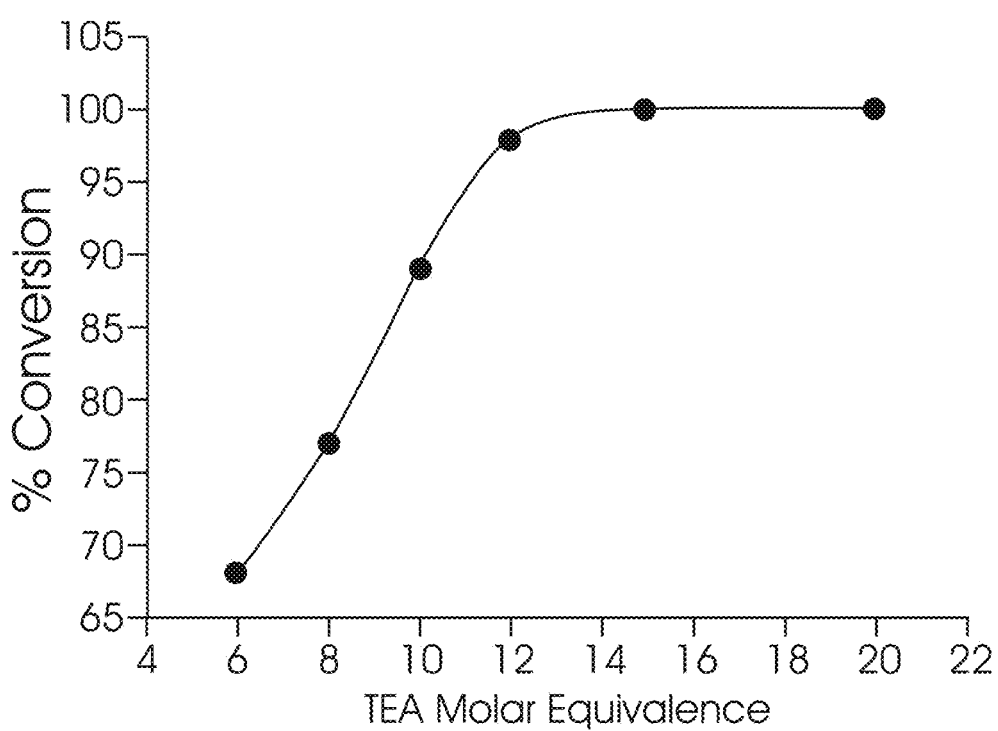
FIG. 9 the effect of base (TEA) molar equivalents on ethyl shikimate conversion.

As can be seen from FIG. 9, ethyl shikimate conversion increased with an increase in base (TEA) concentration. The optimum conditions were found to be ethyl shikimate (0.2 M), MsCl (0.9 M, effectively 1.5 equiv.), TEA (3 M, 15 equiv.) at room temperature and 12 s residence time affording the desired mesylate in 100% conversion. The observations indicated that the reaction could be done even at much lower residence times than 12 s. However, it was difficult to do a comprehensive investigation of lower residence times due to the limitations posed by the syringe pumps available.

The use of bases other than TEA in continuous flow ethyl shikimate mesylation was investigated. A continuous flow system under sonication (FIG. 24) at room temperature and 12 s residence time was used for these experiments. Ethyl shikimate (0.2 M, 1 equiv.) premixed with MsCl (1.5 equiv.) in ethyl acetate was treated with a suitable base (6 equiv.) in a continuous flow system. The results are shown in FIG. 10.

Figure 10:
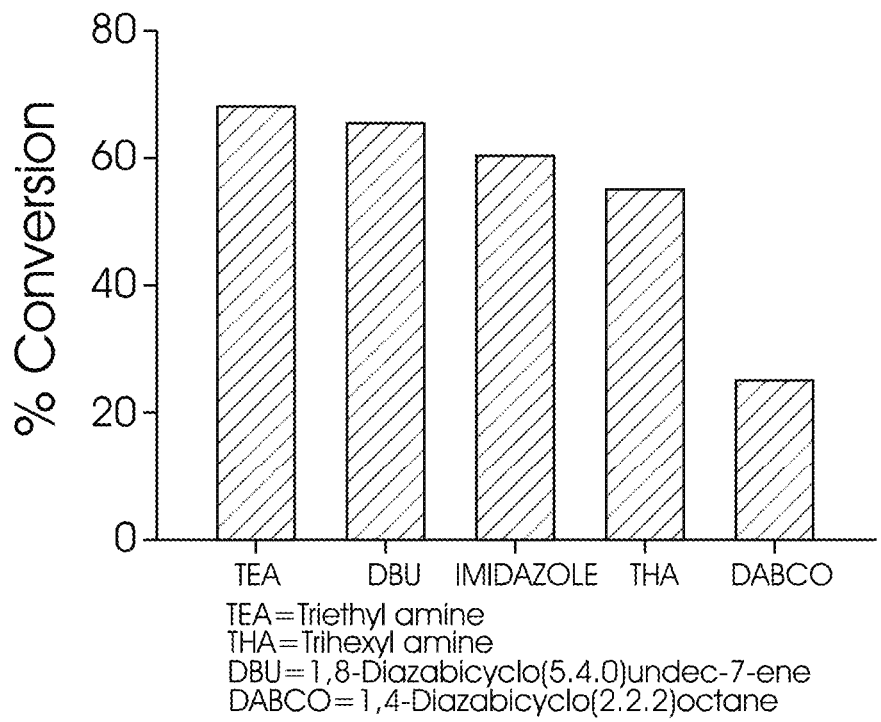
FIG. 10 shows the effect of various bases on continuous flow mesylation.

From FIG. 10, it can be seen that TEA highest conversion of the bases investigated bases, while DABCO performed the worst. Apart from DABCO, all the investigated bases gave results comparable to TEA. Ammonium salt precipitation remained problematic. However, a lighter precipitate was observed with DBU and imidazole. The use of THA interestingly gave a clear solution. The precipitate absence can be attributed to the increase in hydrophobicity (THA) as chain length increased compared to TEA which made the ammonium salt formed soluble in the reaction solvent ethyl acetate.

Reaction 3: Continuous Flow Azidation of Ethyl (3R,-4S,5R)-3,4,5-Tri-O-Methanesulfonylshikimate 40

Figure 25:
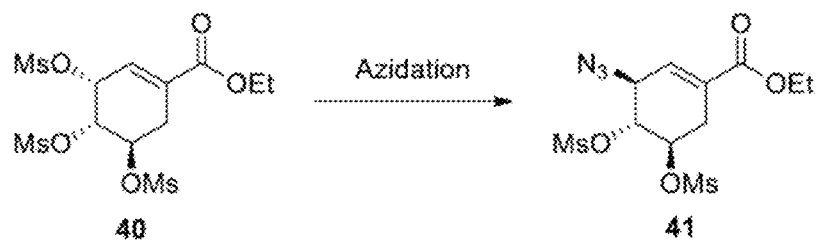
FIG. 25 shows the reaction scheme for the azidation of Ethyl (3R,4S,5R)-3,4,5-Tri-O-Methanesulfonylshikimate 40.

Stereoselective and regioselective nucleophilic substitution of the OMs group at the allylic C-3 position by azido group was done by using different azidating agents and conditions (FIG. 25).

Figure 26:
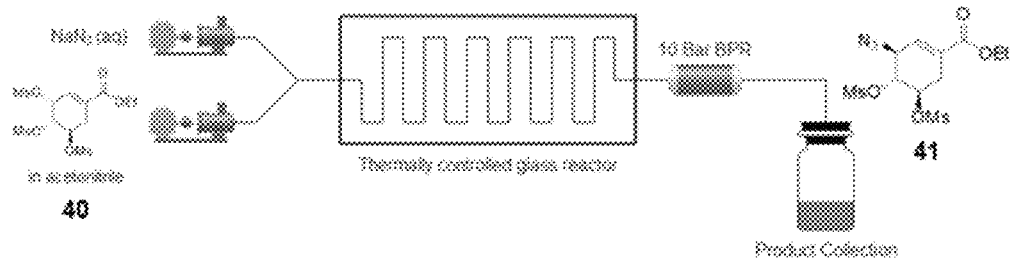
FIG. 26 shows a schematic representation of the continuous flow system used all for the azidation investigations.

Chemtrix's Labtrix start continuous flow system fitted with a 19.5 µl glass reactor was used to optimise the azidation of the OMs group at the allylic C-3 position of mesyl shikimate 40 in the presence of various azidating agents (FIG. 26). Sodium azide (NaN$_3$), diphenylphosphoryl azide (DPPA), trimethylsilyl azide (TMSA) and tetrabutyl ammonium azide (TBAA) were the various azidating agents investigated in this system. The reaction was quenched within the flow reactor using aqueous HCl (0.11 M, 1.1 equiv.) when necessary. Samples were collected and analysed using HPLC method A.

Mesyl shikimate 40 in the presence of a suitable azidating agent undergoes a highly regio- and stereoselective nucleophilic substitution of allylic O-mesylate at the C-3 position affording azide compound 41 (FIG. 25).

Initial experiments had shown the same conversions in both acetone and acetonitrile as mesyl shikimate solvents. However, the use of acetone was associated with eventual micro reactor blockage caused by a resulting precipitate from acetone-aqueous NaN$_3$ mixture. Furthermore, acetonitrile has a higher boiling point than acetone which is desirable for high temperature reaction interrogation. Consequently, acetonitrile was the preferred solvent for mesyl shikimate 40 for further optimisation in continuous flow systems.

Figure 27:
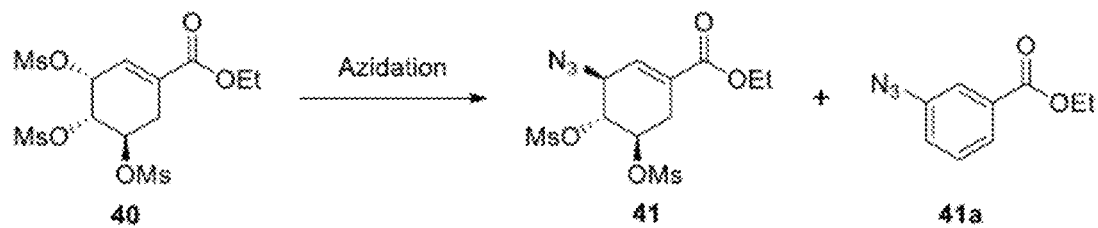
FIG. 27 shows the reaction scheme for the azidation of Ethyl (3R,4S,5R)-3,4,5-Tri-O-Methanesulfonylshikimate 40 in acetonitrile with aqueous $NaN_3$.

Mesyl shikimate 40 (0.1 M) in acetonitrile was treated with aqueous NaN$_3$ (0.11 M, 1.1 equiv.) in a thermally controlled micro reactor system (FIG. 26). The reaction generally affords two products, the desired azide compound 41 and a side product 41a (FIG. 27).

Figure 11:
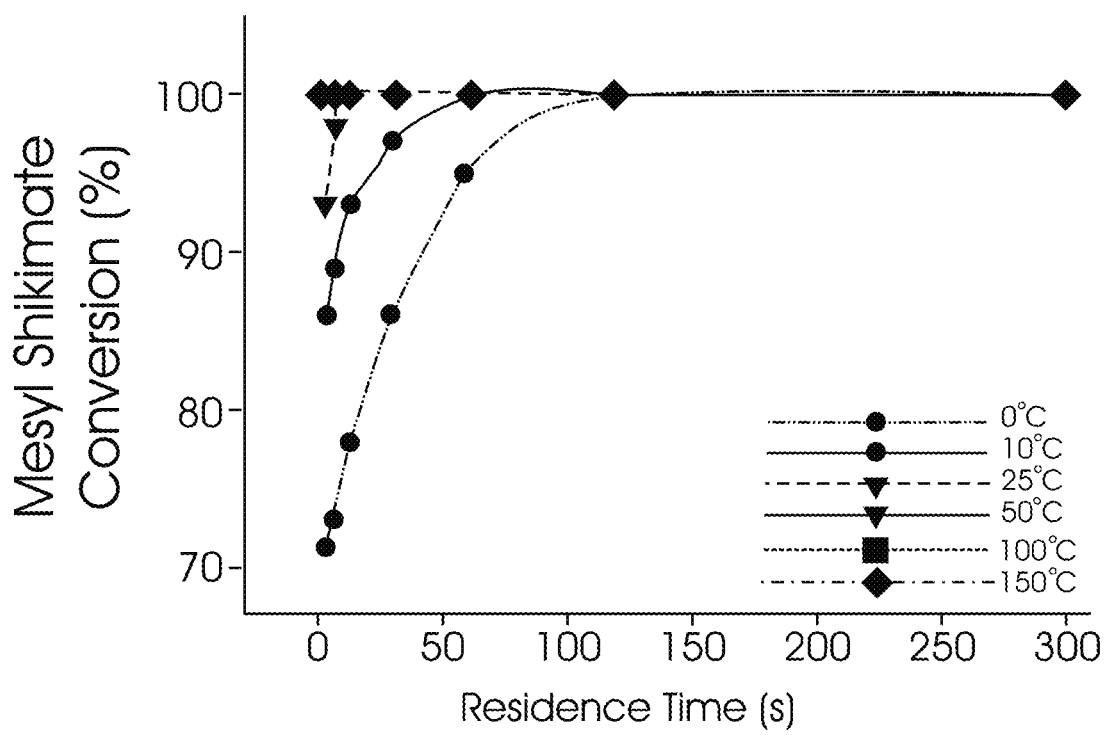
FIG. 11 shows mesyl shikimate azidation conversion in a continuous flow system using $NaN_3$.
Figure 12:
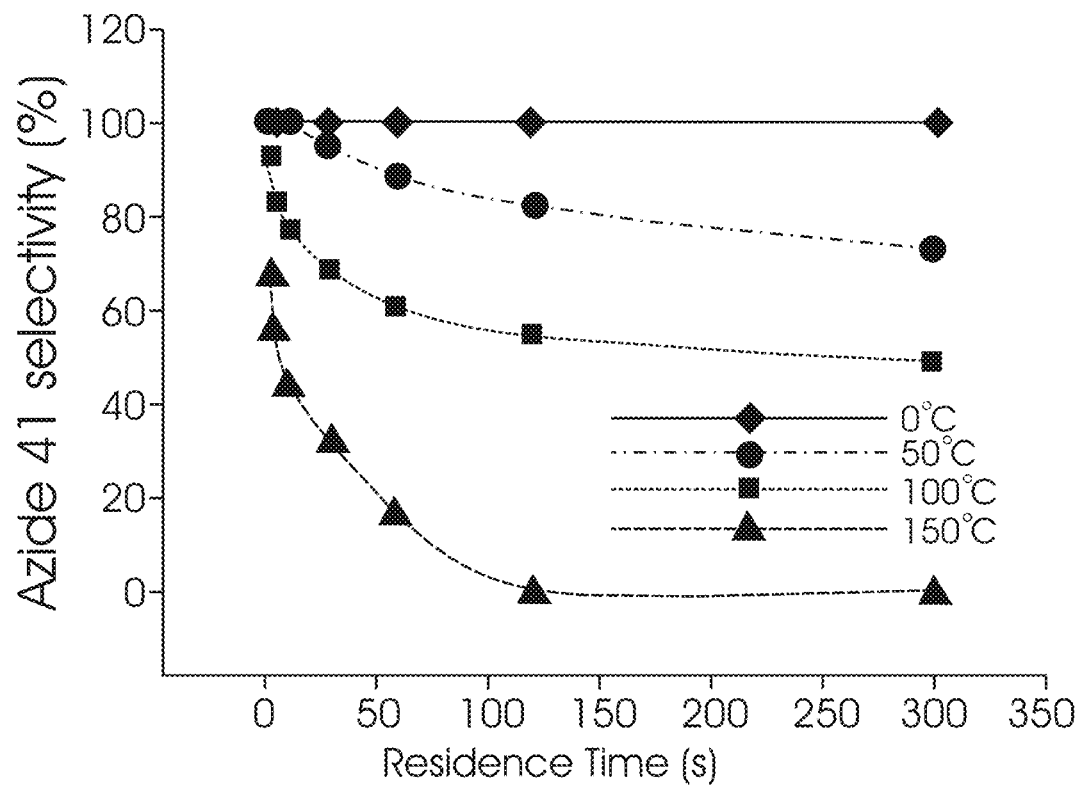
FIG. 12 shows the selectivity towards azide 41 in a continuous flow system using $NaN_3$.

The findings on the effect of various reaction conditions on conversion and selectivity are shown in FIGS. 11 and 12.

From FIG. 11, it is evident that mesyl shikimate conversion increases with increase in residence time and temperature. At 50° C. and above, full conversions were achieved at low residence times. Full conversion was achieved at 50° C., 3 s residence time and 71% conversion at 0° C. and 3 s residence time (FIG. 11).

Product selectivity to azide 41 is shown in FIG. 12. As can be seen from FIG. 12, selectivity generally decreases with increase in residence time and temperature. However, there is 100% selectivity towards the desired azide 41 at 0° C. at all the investigated residence times. At 50° C., 100% and 73% azide 41 selectivity was obtained at 3 s and 300 s respectively. It is evident that high temperatures favour the undesired aromatic azide compound 41a.

The effect of NaN$_3$ concentration on the reaction was investigated, thereby to determine the effect of NaN$_3$ molar equivalent on mesyl shikimate 40 conversion and selectivity of the desired azide 41 at 150° C. and 12 s residence time. Results showed that selectivity towards azide 41 decreases with increase in NaN$_3$ concentration. Contrary, mesyl shikimate 40 conversion improved with an increase in NaN$_3$ (1 and 2 equivalents). It is believed that the excess NaN$_3$ increases reaction basicity, resulting in the undesired azide 41a being exceedingly favoured.

The preferred conditions in flow for this reaction were found to be 1.1 equivalents of NaN$_3$, 50° C. and 12 s residence time affording full conversion to towards the desired azide 41. Despite of high temperatures, long reaction times and basicity being detrimental to the selectivity of the desired azide 41 in batch, as previously reported, it is evident from our experiments that microreactor use significantly improved selectivity let alone massively reducing reaction times.

Alternative, non-aqueous, azidation procedures in continuous flow systems were also investigated. Azidating agents investigated include diphenyl phosphoryl azide (DPPA), trimethylsilyl azide (TMSA), and tetrabutylammonium azide (TBAA).

Mesyl shikimate (0.1 M) was treated with a mixture of DPPA (0.11 M, 1.1 equiv.) and TEA (0.12 M, 1.2 equiv.) in a continuous flow system. The reaction was quenched with aqueous HCl (0.5 M, 0.5 equiv.) within the flow system. Conversion and selectivity results for this reaction is shown in FIGS. 13 and 14.

Figure 13:
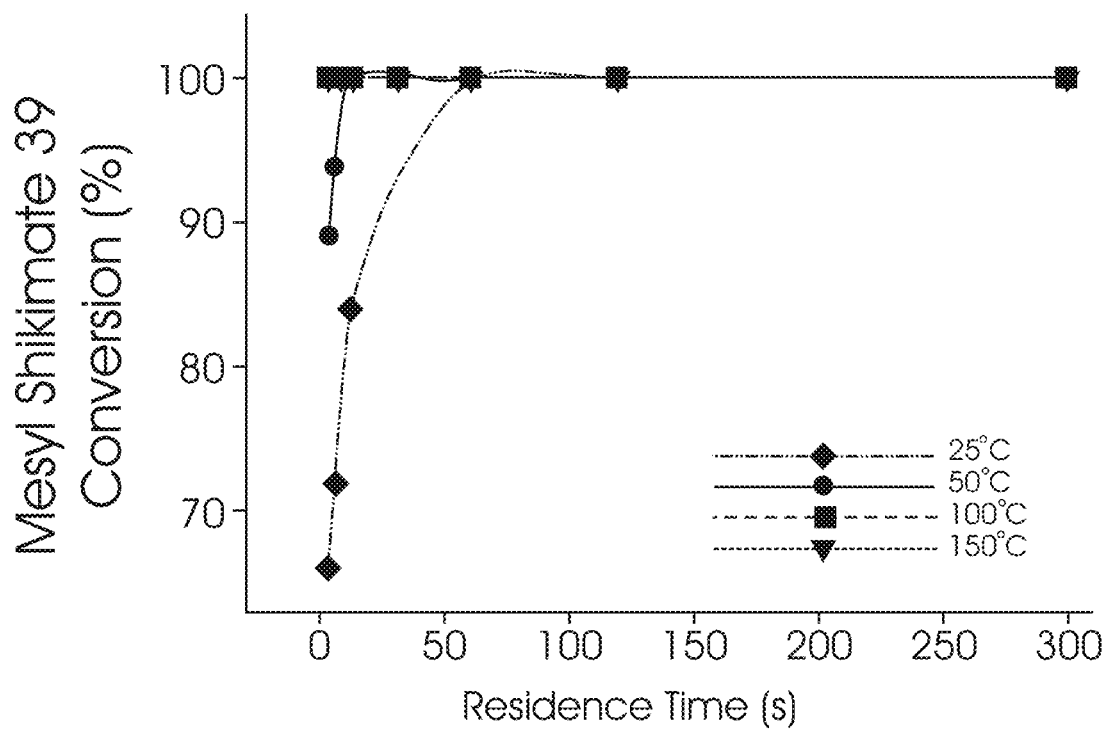
FIG. 13 shows mesyl shikimate azidation conversion in a continuous flow system using DPPA.
Figure 14:
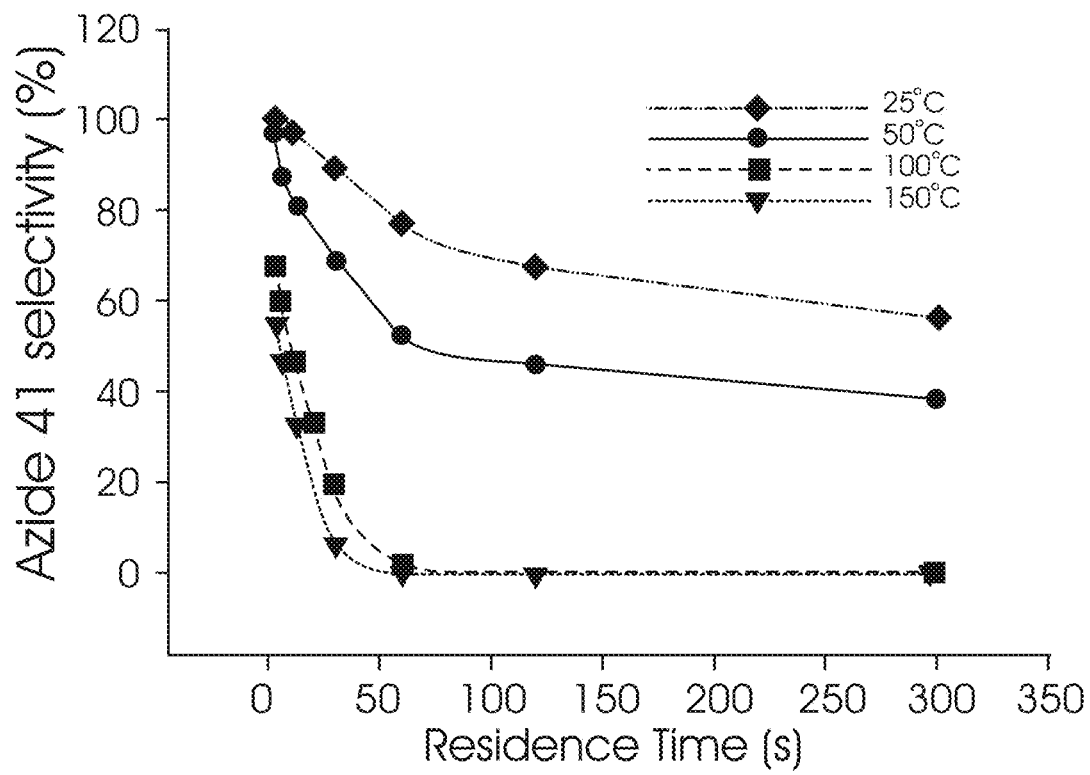
FIG. 14 shows the selectivity towards azide 41 in a continuous flow system using DPPA.

As can be seen from FIG. 13, with DPPA as the azidating agent an increase in both temperature and residence time resulted in the increase in mesyl shikimate conversion in microreactors. Azide 41 selectivity decreases with increase in temperature and residence time (FIG. 14). The trends observed in respect of DPPA were similar to those observed with NaN$_3$ as the azidating agent.

The lower azide 41 selectivity associated with DPPA is as result of the base used. Basic conditions are reportedly detrimental to the azide 41 selectivity. The use of a base in the DPPA procedure was unavoidable as the reaction did not proceed in its absence. The reaction was quenched within the microreactor using aqueous HCl. The effect of base (TEA) concentration on azide 41 selectivity was investigated at room temperature and 6 s residence time to ascertain its role in the formation of the unwanted aromatic azide 41a. Results showed that selectivity towards the desired azide 41 significantly decreased with an increase in base concentration.

The use of TMSA as the azidating agent was also investigated. The conversions found with TMSA were comparable with both NaN$_3$ and DPPA. Mesyl shikimate conversion of 64%, 66% and 71% were obtained at 25° C. and 3 s residence time by using TMSA, DPPA and NaN$_3$ as azidating agents respectively. Azide 41 selectivity using TMSA was also comparable to that obtained with DPPA and NaN$_3$.

Reactions performed with TBAA resulted in unacceptable selectivity towards azide 40, while the use of azide ion exchange reson (Amberlite IRN78) gave comparatively poor conversion performance.

The preferred reaction conditions for the NaN$_3$ procedure were found to be about 1.1 equivalents of NaN$_3$, 50° C. and 12 s affording full conversion towards the desired azide 41. Contrary to all the published literature procedures, side product 41a was not produced using our procedure. The preferred conditions for the anhydrous procedure are about 1.1 equivalents of DPPA/TMSA, about 1.1 equivalents of TEA, 50° C. and 12 s affording about 81% conversion towards the desired azide 41.

Reaction 4: Continuous flow aziridination of Ethyl (3S,4R,5R)-3-Azido-4,5-bis(Methanesulfonyloxy) cycohex-1-enecarboxylate 41

Figure 29:
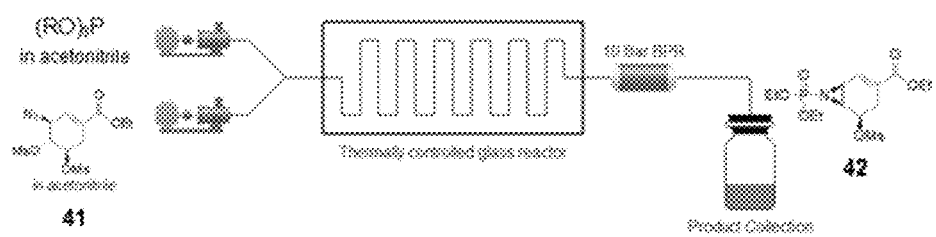
FIG. 29 shows a schematic representation of the continuous flow system used all for the aziridination investigations.

Continuous flow aziridination of azide 41 was done in a Chemtrix Labtrix flow system (FIG. 29).

Chemtrix's Labtrix start continuous flow system fitted with a 19.5 µl glass reactor was used to optimise the aziridination of the azido shikimate 41 using trialkyl phosphite. Triethyl phosphite and trimethyl phosphate were the two alkyl phosphite investigated. A solution of azido shikimate in anhydrous acetonitrile (0.1 M) and a solution of trialkyl phosphite in anhydrous acetonitrile (0.11 M, 1.1 equiv.) were pumped separately using two syringe pumps from two 10 ml SGE Luer lock gas tight glass syringes into the thermally controlled microreactor system which was fitted with a 10 bar back pressure regulator (FIG. 29). Samples were collected and analysed using HPLC method A.

Figure 28:
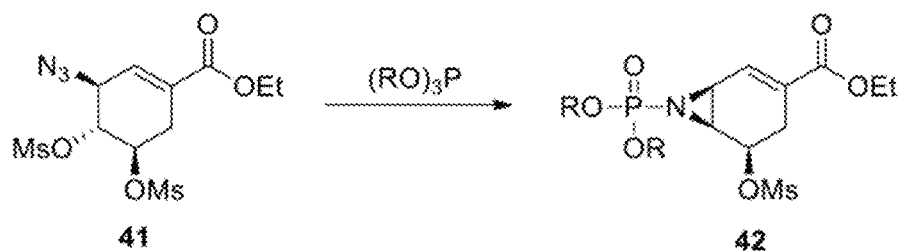
FIG. 28 shows the reaction scheme for the flow aziridination of azide 41.

The azide 41 undergoes aziridination in the presence of trialkyl phosphite under water-free conditions (FIG. 28). In one set of experiments, azide 41 was treated with (EtO)$_3$P under anhydrous conditions in a continuous flow system to afford azidine 42.

Azide 41 (0.1 M) was treated with (EtO)$_3$P (0.11 M, 1.1 equiv.) and spontaneously reacted affording full conversion towards an undesirable product. This was suggestive of an intermediate formation. Experiments were then conducted with acetonitrile as solvent, with the only possible disadvantage of acetonitrile being its lower boiling point, compared to toluene. This was compensated for by pressurising the system, which allowed for reaction superheating without solvent boiling.

Figure 15:
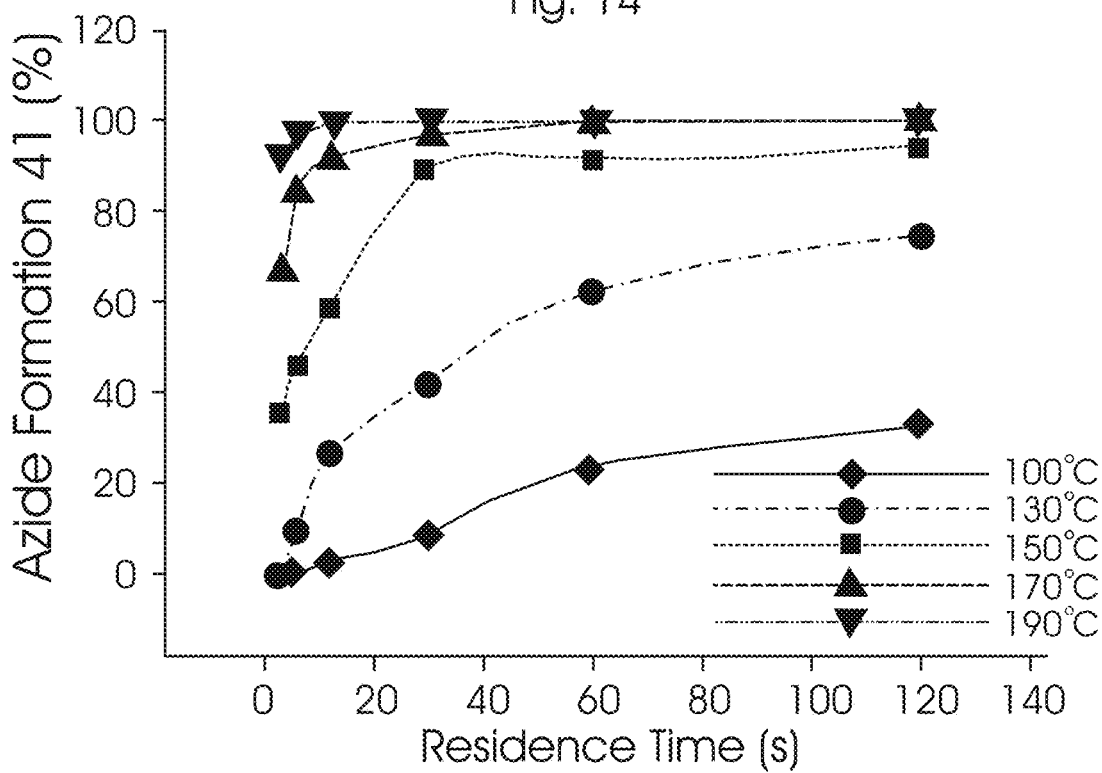
FIG. 15 shows aziridine 42 formation from azide 41 in a continuous flow system with $(EtO)_3P$.

A solution of azide 41 (0.1 M) in acetonitrile was treated with (EtO)$_3$P (0.11 M, 1.1 equiv.) to afford aziridine 42. The conversion of azide 41 to aziridine 42 at various conditions in flow is shown in FIG. 15. Conversion of azide 41 to aziridine 42 in the presence of (EtO)$_3$P increased with increase in temperature and residence time. Good conversion was achieved at very fast residence times (<120 s). Temperature was found to have the most significant effect on the successful synthesis of aziridine 42. As mentioned above, azide 41 was completely consumed in the presence of (EtO)$_3$P at room temperature (toluene), however no aziridine 42 was detected. The use of pressurised microreactors allowed for very high reaction temperatures which resulted in very fast reactions. Furthermore, microreactors allowed safe interrogation of potentially explosive azide chemistry at very high temperatures. Optimum conditions were found to be about 190° C. and 12 s residence time to afford full conversion towards the desired aziridine 42.

In another set of experiments, a continuous flow system was used to perform azide 41 aziridination reaction with (MeO)$_3$P to afford aziridine 42. Results showed that, as with (EtO)$_3$P, aziridine formation increased with increased temperature and residence time. The use of (MeO)$_3$P proved to be slightly more efficient in aziridination than (EtO)$_3$P. At about 190° C. and 3 s residence time, 93% and 98% aziridine 42 was formed using (EtO)$_3$P and (MeO)$_3$P respectively.

Importantly, our system and process allowed for high temperature azide chemistry, resulting in very fast reactions compared to the 5 hour batch reactions previously reported.

Reaction 5: Continuous flow synthesis Ethyl (3R,4S,5R)-4-(Diethoxyphosphorylamino)-5-Methane-Sulfonyloxy-3-(Pent-3-yloxy)Cyclohex-1-Enecarboxylate 43

Figure 30:
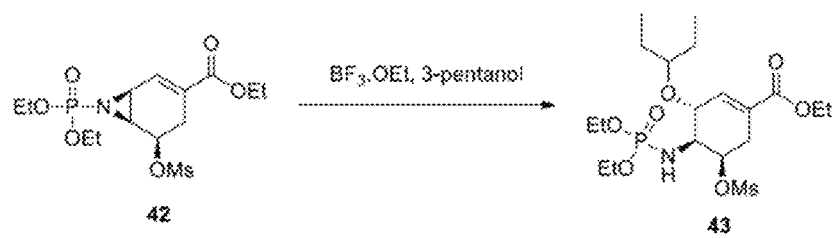
FIG. 30 shows the reaction scheme for the regio- and stereoselective ring opening of aziridine 42 with 3-pentanol and the Lewis catalyst boron trifloride etherate.

The aziridine 42 underwent regio- and stereoselective ring opening with 3-pentanol and the Lewis catalyst boron trifluoride etherate at the allylic position (FIG. 30) in a continuous flow system.

Figure 31:
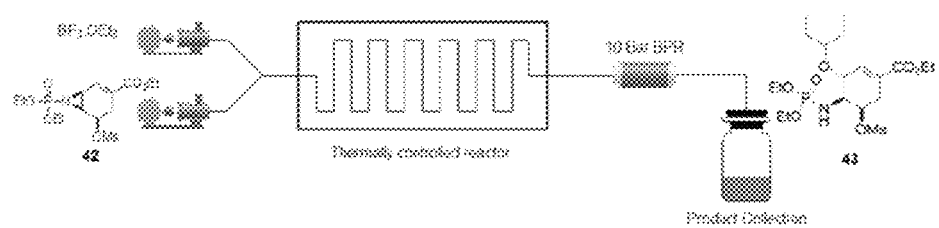
FIG. 31 shows a schematic representation of the continuous flow system used all for the investigation of aziridine 42 ring opening.

Chemtrix's Labtrix start continuous flow system fitted with a 19.5 µl glass reactor was used to optimise the aziridine 42 ring opening with 3-pentanol and boron trifluoride etherate (FIG. 31). The aziridine 42 (0.1 M) in acetonitrile/3-pentanol (50:50) and a solution of boron trifluoride etherate (0.15 M, 1.5 equiv.) in acetonitrile/3-pentanol (50:50) were pumped separately using two syringe pumps from two 10 ml SGE Luer lock gas tight glass syringes into the thermally controlled microreactor system which was fitted with a 10 bar back pressure regulator. Samples were collected and analysed using HPLC method A.

Initial experiments were performed by treating aziridine 42 (0.1 M) in 3-pentanol with BF$_3$·OEt$_2$ (0.12 M, 1.2 equiv.) in 3-pentanol at 60° C. in a continuous flow system for 30 s residence time affording 3-pentyl ether 43 in 88% conversion. The use of an excess of BF$_3$·OEt$_2$ (1.5 equiv.) resulted in full conversion towards 3-pentyl ether 43. Due to pressure build up in the system at higher flow rates, attributed to high viscosity of 3-pentanol, residence times lower than 30 s could not be investigated in this system. Therefore, preliminary investigations at residence times less than 30 s were successfully done by using a 3-pentanol/acetonitrile (50/50) mixture.

The reaction was optimised in a continuous flow system by treating aziridine 42 (0.1 M) in 3-pentanol/acetonitrile (50/50) with BF$_3$·OEt$_2$ (0.15 M, 1.5 equiv.) in 3-pentanol/acetonitrile (50/50) at various reaction conditions. The use of diluted 3-pentanol allowed us to interrogate the reaction at very fast reaction times. Results of these experiments are shown in FIG. 16.

Figure 16:
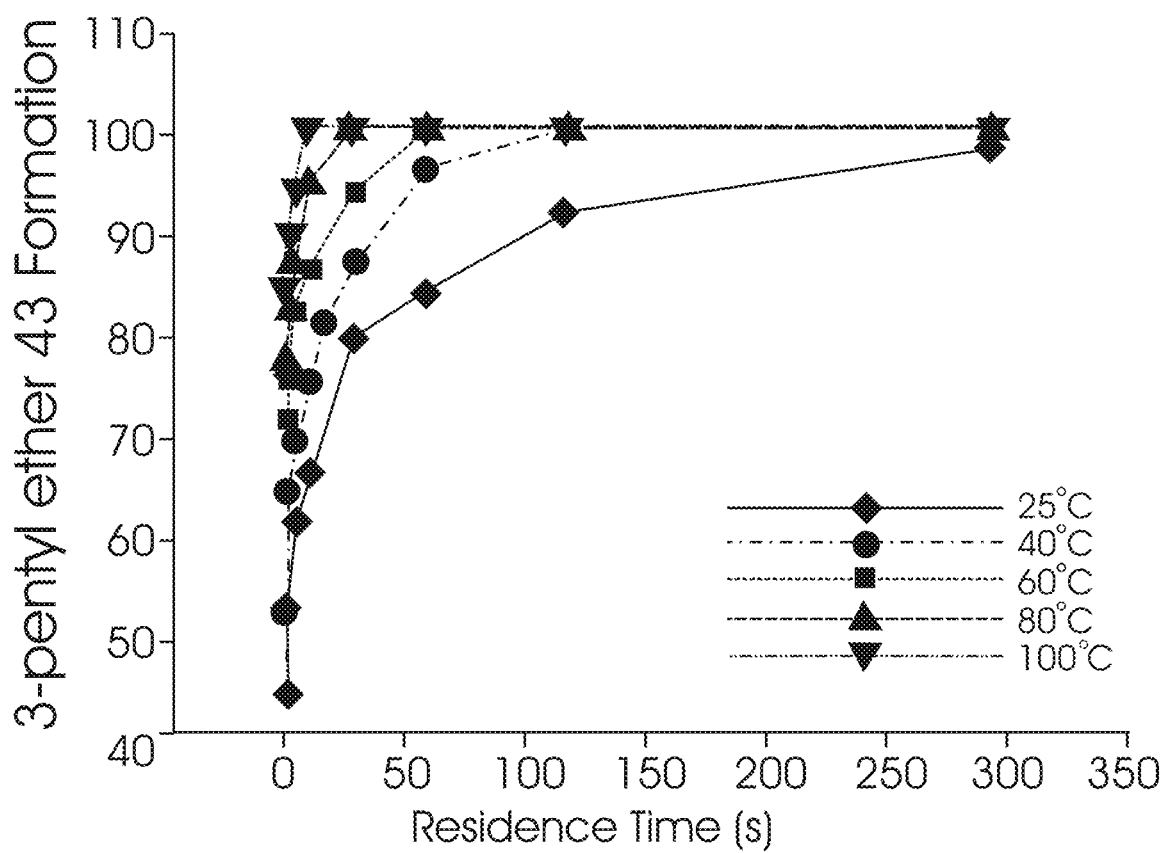
FIG. 16 shows the conversion of 3-pentyl ether 43 from aziridine 42 in a continuous flow system.

As can be seen from FIG. 16, the conversion towards 3-pentyl ether 43 from aziridine 42 increased with increase with residence time and temperature. Temperature increase resulted in a significant improvement in conversion. At 12 s residence time, a 3-pentyl ether 43 yield of 66% and 100% was achieved at 25° C. and 100° C. respectively. The preferred conditions were found to be about 100° C. and 12 s residence time to afford full conversion towards 3-pentyl ether 43.

Reaction 6: Continuous flow synthesis of Ethyl (3R,4S,5R)-4-Acetamido-5-Methanesulfonyloxy-3-(Pent-3-yloxy)Cyclohex-1-Enecarboxylate 44

Figure 32:
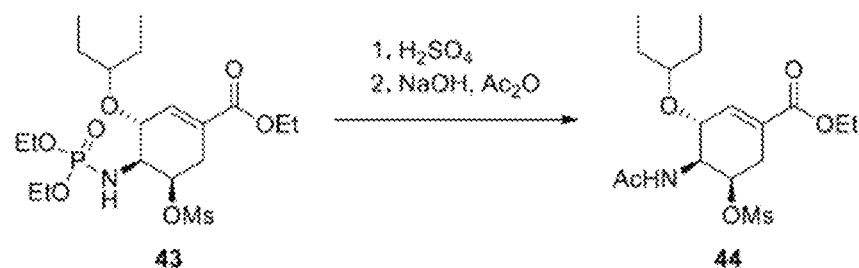
FIG. 32 shows the reaction scheme for the Acetylation of the 3-pentyl ether 43.

Acetylation of the 3-pentyl ether 43 was achieved via N—P bond cleavage with sulphuric acid, followed by acetylation under slightly basic conditions (FIG. 32).

Intermediate 43a was formed in situ in the first thermally controlled reactor by treating the 3-pentyl ether 43 (0.1 M) in acetonitrile with H$_2$SO$_4$ (0.8 M, 8 equiv.) in acetonitrile. The intermediate 43a formed in situ was treated with NaOH (1.62 M, 16.2 equiv.) and then acetic anhydride (1.6 equiv.) in the second thermally controlled reactor to afford acetamide 44. This system for multistep continuous flow system was fitted with a 10 bar back pressure regulator. Samples were collected and analysed using HPLC method A.

Figure 17:
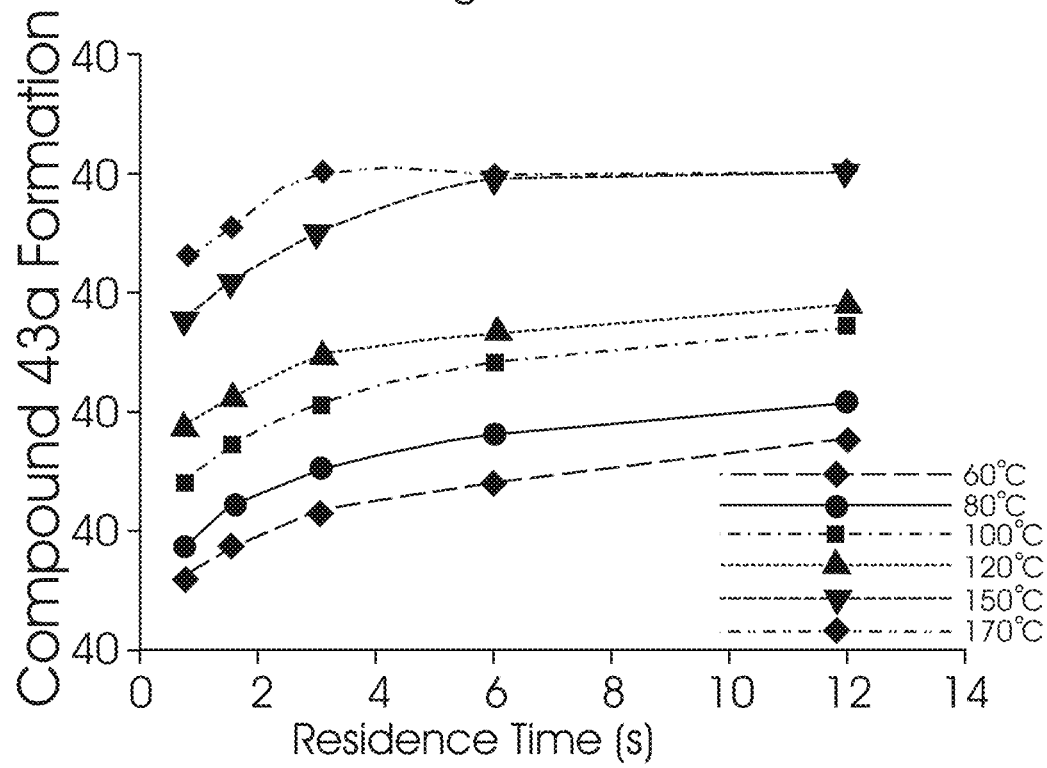
FIG. 17 shows the continuous flow N—P bond cleavage of 3-pentyl ether 43 in a continuous flow system.

In a preliminary set of experiments, 3-pentyl ether 43 (0.1 M) in ethanol was treated with H$_2$SO$_4$ (0.8 M, 8 equiv.) in ethanol at 75° C. and 6 s residence time afforded compound 43a in 51% conversion. Comparable results were obtained when acetonitrile was used as a solvent instead of ethanol. Since acetonitrile was the common solvent for most of the continuous flow steps, the reaction was then optimised in acetonitrile. A solution of 3-pentyl ether 43 (0.1 M) in acetonitrile was treated with a solution of H$_2$SO$_4$ (0.8 M, 8 equiv.) in acetonitrile in a Chemtrix microreactor at various reaction conditions for optimisation. The results of these experiments are shown in FIG. 17.

The conversion of 3-pentyl ether 43 to compound 43a increased with increase in temperature and residence time. Conversion towards compound 43a was 37% and 91% at 60° C. and 150° C. respectively at 1.5 s residence time. At constant temperature of 60° C., conversion towards compound 43a was 31% and 54% at 0.7 s and 12 s respectively. The preferred conditions for continuous flow N—P bond cleavage were found to be about 170° C. and 3 s residence time using H₂SO₄ (8 equiv.) to afford compound 43a in full conversion.

Having successfully demonstrated the continuous flow N—P bond cleavage in 3-pentyl ether 43 afford compound 43a, the investigation was extended to acetylation of compound 43a.

Figure 33:
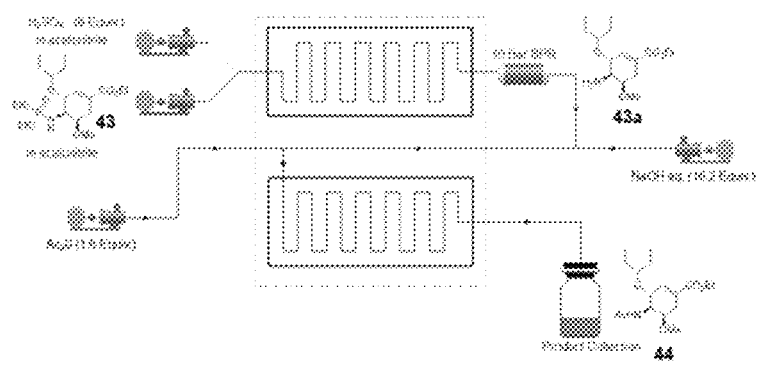
FIG. 33 shows a schematic representation of the continuous flow system used all for the acetylation investigations.

The acetylation of 3-pentyl ether 43 was completed by subsequently treating the compound 43a formed in situ with Ac₂O under slightly basic conditions to afford acetamide 44 in a continuous flow system (FIG. 33). Based on results from previous experiments, 3-pentyl ether 43 (0.1 M) in acetonitrile was treated with H₂SO₄ (8 equiv.) in acetonitrile at 170° C. in the first microreactor for 6 s residence time to afford compound 43a in situ which was subsequently treated with an aqueous NaOH (0.8 M, 16.2 equiv.) and subsequently with Ac₂O (0.8 M, 1.6 equiv.) at room temperature to afford acetamide 44 (65%) at 9 s total residence time.

Increase in total residence time for acetylation resulted in increase in acetamide 44 formation. Doubling the total residence time resulted in a 12% conversion increase. Total residence time of 30 s gave 93% acetamide 44 and there was no conversion improvement beyond 30 s residence time. As in the preceding steps, basic reaction medium could have caused side reactions thus lowering acetamide 44 yield. The basic reaction medium is attributed to the slightly basic medium used to facilitate acetylation and the basicity of intermediate 43a formed in situ.

Reaction 7: Continuous Flow Synthesis of (3R,4S, 5S)-5-Azido-4-Acetylamino-3-(1-Ethyl-Propoxy)-Cyclohex-1-Enecarboxylic Acid Ethyl Ester 32

Figure 34:
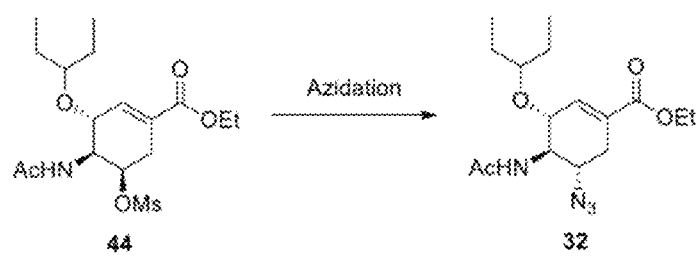
FIG. 34 shows the reaction scheme for the treatment of Acetamide 44 with a suitable azidating agent to afford Azide 32.

Acetamide 44 is treated with a suitable azidating agent to afford azide 32. The C-5 OMs group on acetamide 44 undergoes nucleophilic replacement by the N₃ group (FIG. 34).

Figure 35:
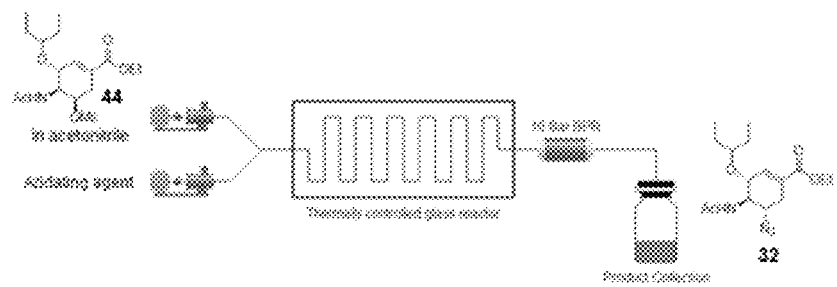
FIG. 35 shows a schematic representation of the continuous flow system used all for the azidation investigations.
Figure 36:
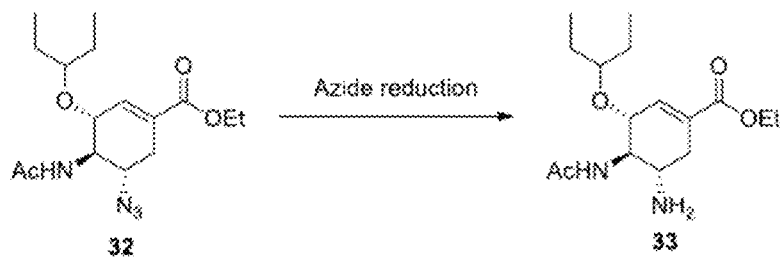
FIG. 36 shows the reaction scheme for azide reduction of Azide 32.

Chemtrix's Labtrix start continuous flow system fitted with a 19.5 μl glass reactor was used to optimise the C-5 azidation of acetamide 44 (FIG. 35). The acetamide 44 (0.1 M) in acetonitrile and azidating agent in appropriate solvent (0.3 M, 3 equiv.) were pumped separately using two syringe pumps from two 10 ml SGE Luer lock gas tight glass syringes into the thermally controlled microreactor system which was fitted with a 10 bar back pressure regulator. The use of NaN₃, TBAA, DPPA, and TMSA were investigated. Samples were collected and analysed using HPLC method A.

Initial experiments in flow were done using acetamide 44 (0.1 M) in DMF and aqueous NaN₃ (0.3 M, 3 equiv.) in a 19.5 μl glass microreactor at 100° C. for 90 s affording azide 32 (63%). In other experiments we achieved 59% conversion to azide 32 in acetonitrile. The reaction was further optimised using acetonitrile as acetamide 44 (0.1 M) solvent and aqueous NaN₃ (0.1 M, 3 equiv.). The results of these experiments are shown in FIG. 18.

Figure 18:
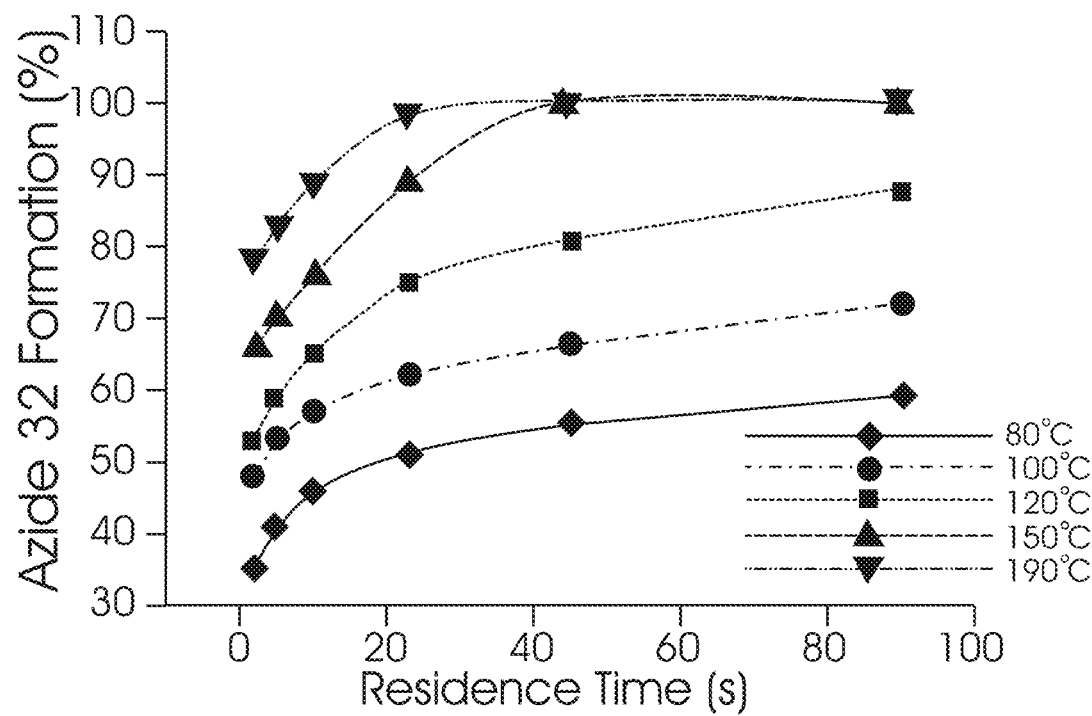
FIG. 18 shows the C-5 azidation of acetamide 44 using $NaN_3$ in a continuous flow system.

As can be seen from FIG. 18, azide 32 formation is a function of temperature and residence time. The conversion of acetamide 44 to azide 32 increased with increase temperature. Conversion towards azide 32 was 55% and 100% at 80° C. and 190° C. at 45 s residence time respectively. The preferred conditions were found to be about 190° C., 45 s residence time to afford azide 32 in full conversion.

Preferred conditions developed for NaN₃ (3 equiv., 190° C., and 45 s) were used to investigate the use DPPA, TMSA and TBAA as azidating agents for acetamide 44 in a 19.5 μl glass microreactor. In these experiments, acetamide 44 was successfully converted to azide 32 at varying conversions DPPA, TMSA, and TBAA. It appears that the application of ionic bonded azides (NaN₃ and TBAA) gave similar conversions (100% and 93% respectively), whilst covalently bonded azides (DPPA and TMSA) resulted in comparativelt lower conversions (84% and 81% respectively).

Reaction 8: Continuous Flow Synthesis of Oseltamivir 33

Figure 37:
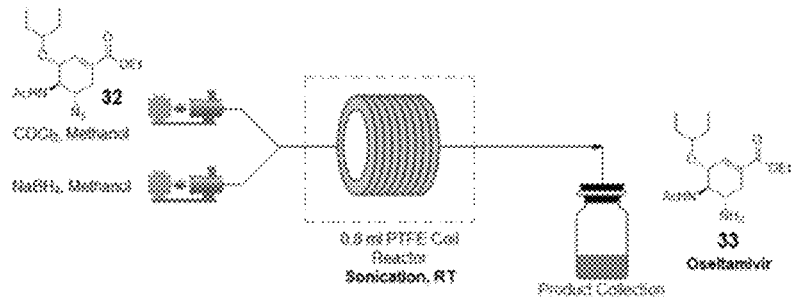
FIG. 37 shows a schematic representation of the continuous flow system used all for the azide reduction investigations.

A 0.8 ml PTFE coil reactor (0.8 mm ID, 1.6 m tube length) under sonication (FIG. 37) was used to optimise the azide 32 reduction to afford Oseltamivir using NaBH₄ and CoCl₂. A mixture of azide 32 (0.15 M) with CoCl₂ (0.1 equiv.) in ethanol and NaBH₄ (0.30 M, 2 equiv.) in water (pH=8) was pumped through the continuous flow system to afford Oseltamivir 33. The samples collected were first filtered through a PTFE syringe filter (0.45 μl pore size) to remove the cobalt boride precipitates formed in the reaction, and then analysed using HPLC method A.

Oseltamivir 33 was synthesised from CoCl₂ catalysed NaBH₄ reduction of azide 32 in a continuous flow system under sonication because the formation of a black precipitate (cobalt boride) was observed in preliminary batch-type investigations. However, it is possible that the formation of this precipitate may not be problematic when the method is performed using industrial scale equipment.

Figure 19:
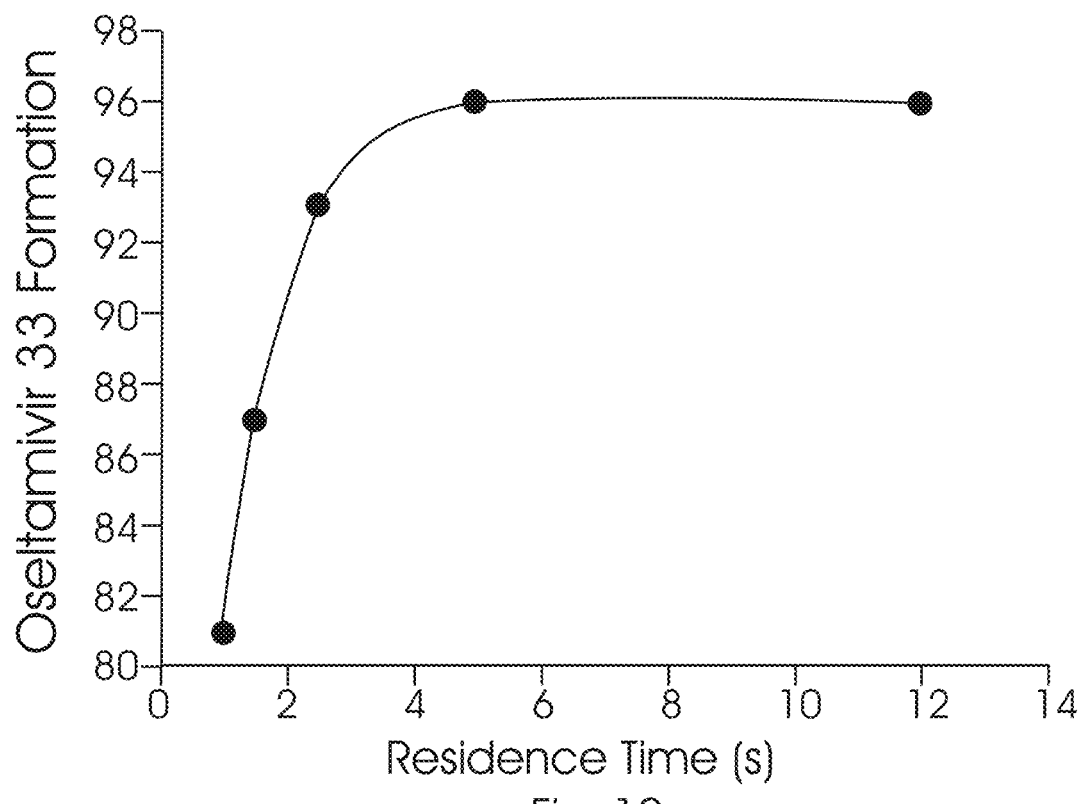
FIG. 19 shows Oseltamivir 33 synthesis from azide 32 using $CoCl_2$ catalysed $NaBH_4$ reduction in a continuous flow system.

A mixture of azide 32 (0.15 M) with CoCl₂ (0.1 equiv.) in ethanol was treated with NaBH₄ (0.3 M, 2 equiv.) in buffered water (pH=8) in a 0.8 ml PTFE coil reactor system (0.8 mm ID, 1.6 m tube length) under sonication to afford oseltamivir 33. The results of these experiments are shown in FIG. 19. Conversion towards Oseltamivir 33 increased with increase in residence time. Conversion towards oseltamivir 33 was unexpectedly found to be 81% and 96% at residence times of only 1 s and 5 s respectively. The preferred conditions were found to be about room temperature and a residence time of about 5 s to afford Oseltamivir 33 (96%).

We also conducted experiments to investigate the use of ethanol and methanol for NaBH₄. These experiments were done at room temperature for 1.5 s residence time in a sonicated continuous flow system. Although ethanol and methanol are known to react with NaBH₄, it appears that the azide reduction reaction, in the presence of a catalytic amount of CoCl₂, is so fast that it overshadows the competing reactions by these solvents. Therefore, although water at ph>7 is preferred, it is anticipated that several other solvents will also be suitable.

In other experiments, as suggested in known batch methods, a phosphine based reaction was attempted in flow by treating azide 32 (0.15 M) in THF with Ph₃P (0.18 M, 1.2 equiv.) in THF/water (10:1) in continuous flow system at 50° C. to afford Oseltamivir 33. The conversion of azide 32 towards Oseltamivir 33 was 25% and 78% at 5 min and 60 min residence time respectively, which is much lower than that obtained in the preferred reaction with CoCl₂ and NaBH₄.

Reaction 8: Continuous Flow Synthesis of Oseltamivir Phosphate 3

Figure 38:
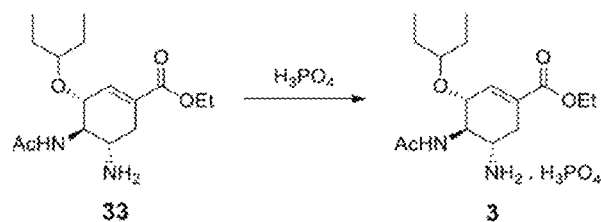
FIG. 38 shows the reaction scheme for the conversion of Oseltamivir 33 to Oseltamivir phosphate 3.
Figure 39:
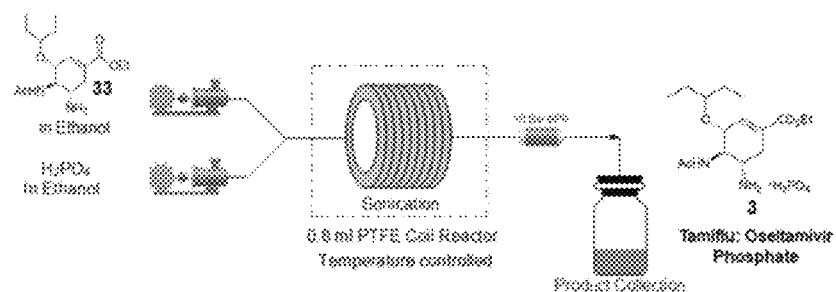
FIG. 39 shows a schematic representation of the continuous flow system used all for the investigations relating to the conversion of Oseltamivir 33 to Oseltamivir phosphate 3.

Oseltamivir 33 was treated with H₂PO₄ to afford Oseltamivir phosphate 3 (FIG. 38) in a continuous flow system.

A 0.8 ml PTFE coil reactor (0.8 mm ID, 1.6 m tube length) under sonication was used to optimise the treatment of Oseltamivir 33 with H₂PO₄ affording Oseltamivir phosphate 3 in a continuous flow system. Oseltamivir 33 (0.1 M) in ethanol and H₂PO₄ (0.12 M, 1.2 equiv.) in ethanol were pumped through a thermally controlled continuous flow system to afford oseltamivir phosphate. Samples were collected and analysed using HPLC method A.

Figure 20:
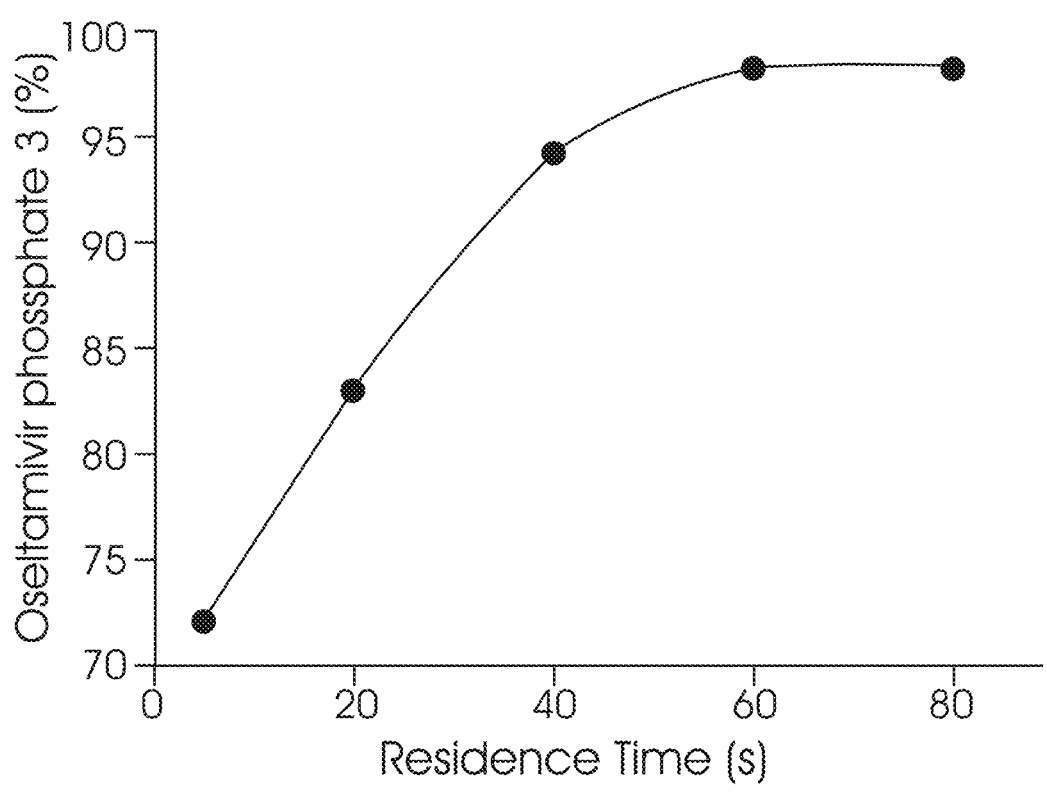
FIG. 20 shows the conversion of Oseltamivir phosphate 3 from Oseltamivir 33 in a continuous flow system.

Oseltamivir 33 (0.1 M) in ethanol was treated with $H_2PO_4$ (0.12 M, 1.2 equiv.) in ethanol at 50° C. in a 0.8 ml PTFE coil reactor (0.8 mm ID, 1.6 m tube length) under sonication at various residence times for optimisation. The results of these experiments are shown in FIG. 20.

Conversion to Oseltamivir phosphate 3 increased with increase in residence time. A conversion plateau of 98% (HPLC) towards Oseltamivir phosphate 3 was reached at 60 s residence time. Based on these experiments, the preferred conditions were about 50° C. and 60 s residence time to give Oseltamivir phosphate 3 (98%, HPLC), which is a significant improvement an any previously reported reaction.

This above description of some of the illustrative embodiments of the invention is to indicate how the invention can be made and carried out. Those of ordinary skill in the art will know that various details may be modified thereby arriving at further embodiments, but that many of these embodiments will remain within the scope of the invention.

The invention claimed is:
1. A flow synthesis process for producing a compound of the Formula 33 and its pharmaceutically acceptable salts,

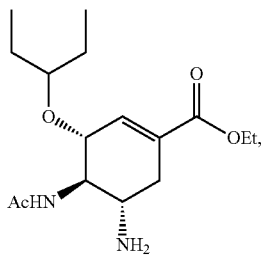

33 the process comprising the steps of:
a) preparing ethyl shikimate of Formula 39

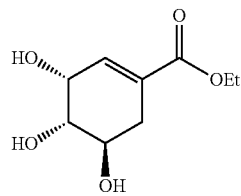

39 by reacting shikimic acid with a reagent selected from the group consisting of $(COCl)_2$, $SOCl_2$, benzene sulphonic acid (BSA), p-toluene sulphonic acid (PTSA), and Amberlyst 15,
b) reacting the ethyl shikimate of Formula 39 with mesyl chloride in the presence of a base selected from the group consisting of trimethyl amine (TEA), 1,8-diazabicyclo(5.4.0) undec-7-ene (DBU), imidazole, and trihexyl amine (THA) to produce the O-trimesylate of Formula 40, wherein the base is present at a concentration of about 8 to about 20 molar equivalents relative to ethyl shikimate,

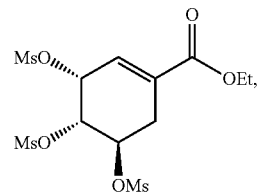

40 c) reacting the O-trimesylate of Formula 40 in an azidation reaction with an appropriate azidating agent to produce the azide of Formula 41

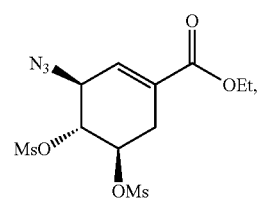

41 d) reacting the azide of Formula 41 in an aziridation reaction with a trialkyl phosphite to produce the aziridine of Formula 42

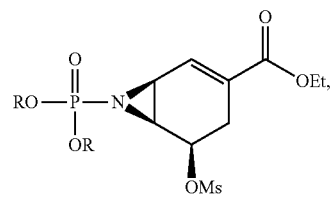

42 e) reacting the aziridine of Formula 42 with 3-pentanol in the presence of a Lewis acid catalyst to produce the 3-pentyl ether of Formula 43

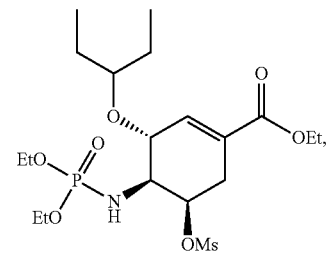

43 f) reacting the 3-pentyl ether of Formula 43 in an acetylation reaction with $H_2SO_4$, followed by $Ac_2O$ in the presence of a suitable base to produce the acetamide of Formula 44

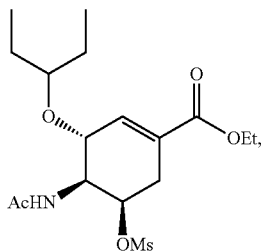

44 g) reacting the acetamide of Formula 44 in an azidation reaction with an appropriate azidating reagent produce the azide of Formula 32

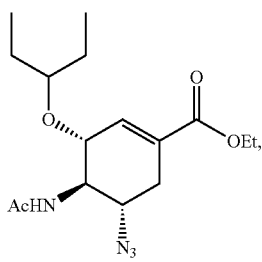

32 and h) reacting the azide of Formula 32 by mixing the azide with $CoCl_2$, and reacting the mixture with $NaBH_4$ to produce the compound of Formula 33.

2. The process according to claim 1, further comprising reacting the compound of Formula 33 with phosphoric acid to produce the compound of Formula 3

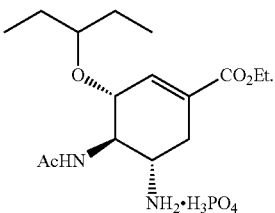

3

3. The process according to claim 1, wherein in step (a) shikimic acid is reacted with $(COCl)_2$ or Amberlyst 15.

4. The process according to claim 1, wherein in step (a) shikimic acid is reacted with $(COCl)_2$ at a temperature of between about 120° C. and about 170° C.

5. The process according to claim 1, wherein in step (a) shikimic acid is reacted with Amberlyst 15 at a temperature of between about 100° C. and about 145° C.

6. The process according to claim 1, wherein the reaction in step (b) proceeds at room temperature.

7. The process according to claim 1, wherein the reaction in step (b) proceeds under sonication.

8. The process according to claim 1, wherein in step (c) the azidation reaction is performed with $NaN_3$ at a concentration of about 1.1 molar equivalents relative to the O-trimesylate of Formula 40.

9. The process according to claim 1, wherein in step (c) the azidation reaction is performed with $NaN_3$ at a temperature of about 50° C.

10. The process according to claim 1, wherein in step (d) the trialkyl phosphite is selected from triethyl phosphite and trimethyl phosphite.

11. The process according to claim 1, wherein in step (d) the reaction is performed in acetonitrile at a temperature of between about 150° C. to about 190° C.

12. The process according to claim 1, wherein in step (e) the reaction is performed at a temperature of between about 60° C. to about 100° C.

13. The process according to claim 1, wherein in step (f) the reaction of the 3-pentyl ether with $H_2SO_4$ is performed at a temperature of between about 140° C. to about 180° C.

14. The process according to claim 1, wherein in step (g) the reaction is performed at a temperature of between about 140° C. to about 200° C.

15. The process according to claim 1, wherein in step (h) the reaction is performed at about room temperature.

16. The process according to claim 1, wherein in step (h) the reaction is performed under sonication.

17. The process according to claim 6, wherein the reaction in step (b) proceeds under sonication.

18. The process according to claim 8, wherein in step (c) the azidation reaction is performed with $NaN_3$ at a temperature of about 50° C.

19. The process according to claim 10, wherein in step (d) the reaction is performed in acetonitrile at a temperature of between about 150° C. to about 190° C.

20. The process according to claim 13, wherein in step (h) the reaction is performed under sonication.

\* \* \* \* \*